(12) United States Patent
Thiemermann

(10) Patent No.: US 9,603,831 B2
(45) Date of Patent: Mar. 28, 2017

(54) ARTEMISININ AND ITS DERIVATIVES FOR USE IN THE TREATMENT OF KIDNEY DISEASE

(71) Applicant: Queen Mary & Westfield College, University of London, London (GB)

(72) Inventor: Christoph Thiemermann, London (GB)

(73) Assignee: Queen Mary & Westfield College, University of London, London (GB)

( * ) Notice: Subject to any disclaimer, the term of this patent is extended or adjusted under 35 U.S.C. 154(b) by 0 days.

(21) Appl. No.: 14/651,298

(22) PCT Filed: Dec. 12, 2012

(86) PCT No.: PCT/EP2012/075306
§ 371 (c)(1),
(2) Date: Jun. 11, 2015

(87) PCT Pub. No.: WO2014/090306
PCT Pub. Date: Jun. 19, 2014

(65) Prior Publication Data
US 2015/0335612 A1 Nov. 26, 2015

(51) Int. Cl.
*A61K 31/357* (2006.01)
*A61M 1/28* (2006.01)
(Continued)

(52) U.S. Cl.
CPC .......... *A61K 31/357* (2013.01); *A01N 1/0226* (2013.01); *A61K 35/22* (2013.01); *A61M 1/287* (2013.01); *G01N 33/70* (2013.01)

(58) Field of Classification Search
CPC .... A61K 31/357; A61K 35/22; A01N 1/0226; A61M 1/287; G01N 33/70
(Continued)

(56) References Cited

U.S. PATENT DOCUMENTS

2008/0139641 A1 6/2008 Meyer
2008/0139642 A1 6/2008 Li et al.
(Continued)

FOREIGN PATENT DOCUMENTS

CN 102552908 * 7/2012
WO 0004026 1/2000
(Continued)

OTHER PUBLICATIONS

Wu et al, Establishment of mice nephritis models and observation of effects of dihydroartemisinin on release of inflammatory cytokines, Huaxi Yixue, 2011, 26(7), p. 1028-1031, abstract page.*
(Continued)

*Primary Examiner* — T. Victor Oh
(74) *Attorney, Agent, or Firm* — Stradley Ronon Stevens & Young, LLP

(57) ABSTRACT

The present invention relates compounds according to Formula (I) wherein $R^1$ and $R^2$ are independently H or an optionally substituted group selected from an alkyl, a heteroalkyl, an aryl, a heteroaryl, an arylalkyl, and a heteroarylalkyl, and $R^3$ and $R^4$ taken together form a carbonyl (=O); or wherein $R^1$ and $R^2$ are independently H or an optionally substituted group selected from an alkyl, a heteroalkyl, an aryl, a heteroaryl, an arylalkyl, and a heteroarylalkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or pharmaceutically acceptable salts or esters thereof, for use in the treatment of kidney disease, in particular in the treatment of acute kidney injury. The present invention also relates to methods of treatment of the same and methods of kidney transplant surgery and coronary artery bypass graft surgery using the compounds of Formula (I).

(Continued)

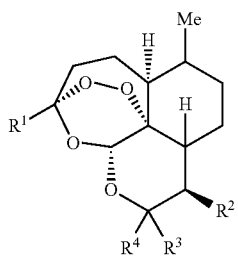

(I)

24 Claims, 9 Drawing Sheets

(51) Int. Cl.
  A01N 1/02 (2006.01)
  A61K 35/22 (2015.01)
  G01N 33/70 (2006.01)
(58) Field of Classification Search
  USPC .......................................................... 514/302
  See application file for complete search history.

(56) References Cited

U.S. PATENT DOCUMENTS

| 2010/0137246 A1 | 6/2010 | Hyde et al. |
| 2011/0077258 A1 | 3/2011 | Carvalho et al. |

FOREIGN PATENT DOCUMENTS

| WO | 2004028476 A2 | 4/2004 |
| WO | 2007125397 A2 | 11/2007 |
| WO | 2008005276 A2 | 1/2008 |
| WO | 2010110747 A1 | 9/2010 |
| WO | 2010132821 A2 | 11/2010 |
| WO | 2010135427 A2 | 11/2010 |
| WO | 2012033266 A1 | 3/2012 |
| WO | 2012168450 A1 | 12/2012 |

OTHER PUBLICATIONS

Mishra et al, Acute Renal Failure in Falciparum Malaria, JIACM, 2002, 3(2), p. 141-147.*
Anyasor et al., Evaluation of selected biochemical parameters in renal and hepatic functions following oral administration of artesunate to albino rats, Resaercher 2011 3(7):30-34.
Bellomo et al., Acute kidney injury, Lancet 2012 380:756-66.
Bellomo et al., Acute renal failure—definition, outcome measures, animal models, fluid therapy and information technology needs: the second international consensus conference of the acute dialysis quality initiative (ADQI) group, Critical Care 2004 8:R204-12.
Campos et al., Effects of sodium artesunate, a new antimalarial drug, on renal function, Kidney Int. 2001 59 (3):1044-51.
Halloran, Immunosuppressive drugs for kidney transplantation, N Eng J Med 2004 351:2715-29.
International Search Report and Written Opinion dated Mar. 1, 2013 for International Application No. PCT/EP2012/075306.
Johnson et al., The delayed administration of IKK-16, a specific iKKbeta inhibitor, attenuates acute kidney injury in rat recovery model of unilateral renal ischaemia, BPS Winter Meeting London 2012.
Li et al., Antimalarial artesunate protects sepsis model mice against heat-killed *Escherichia coli* challenge by decreasing TLR4, TLR9 mRNA expressions and transcription factor NF-kappaB activation, International Immunopharmacology 2008 8:379-79.
Mirshafiey et al., Therapeutic effect of artemether in an experimental model of nephrosis, Pharmaceutical Biology 2008 46(9):639-46.
Nankivell et al., Rejection of the kidney allograft, N Eng J Med 2010 363:1451-62.
Pascual et al., Strategies to improve long-term outcomes after renal transplantation, N Eng J Med 346(8):580.
Sun et al., Effect of artemisinin on ischemia/reperfusion injury of isolated rat myocardium, Zhongguo Zhongyao Zazhishe 2007 32(15):1547-51.
Wang et al., Effect of artesunate on endotoxin-induced uveitis in rats, Investigative Ophthalmology & Visual Science 2011 52(2):916-9.
Wu et al., Effect of artemisinin combined with glucocorticoid on the expressions of glucocorticoid receptor alpha mRNA, glucocorticoid receptor beta mRNA and P300/CBP protein in lupas nephritis mice, Chin J Integr Med 2011 17 (4):277-82.
Wu et al., Therapeutic effect of artemisinin on lupus nephritis mice and its mechanisms, Acta Biochem Bioshys Sin 2010 42:916-23.
Aldieri et al., Artemisinin inhibits inducible nitric oxide synthase and nuclear factor NF-kB activation, FEBS Letters 2003 552:141-144.
Gohil et al., Nutrient-sensitized screening for drugs that shift energy metabolism from mitochondrial respiration to glycolysis, Nature Biotech 2010 28(3):249.
Golenser et al., Current perspectives on the mechanism of action of artemisinins, International Journal Parasitology 2006 36:1427-1441.
Hierholzer et al., Essential role of induced nitric oxide in the initiation of the inflammatory response after hemorrhagic shock, J Exp Med 1998 187(6):917-928.
Kozikowski et al. (2011): STN International, HCAPLUS database (Columbus, OH), Accession No. 2011:108897.
Mootha et al. (2010): STN International, HCAPLUS database (Columbus, OH), Accession No. 2010:1433046.
Office Action dated Jun. 7, 2016 issued in U.S. Appl. No. 14/125,032.
Respiratory arest: respiratory arrest and cardiac arrest: Merck Manual 18th Edition Japanese version; Jul. 14, 2016; retreived from the internet http://marckmanual.jp/mmpej/sec06/ch064/ch064b.html.
Shock: Shock and Fluid Resuscitation: Merck Manual 18th Edition Japanese Version; retreived from the internet, Jul. 14, 2016, http://merckmanual.jp/mmpej/sec06/ch067/ch067b.html.
Thiele et al. (2009): STN International, HCAPLUS database (Columbus, OH), Accession No. 2009:143447.
Yasuhara and Date, Regenerative medicine for traumatic brain injury, Japan J Neurosurg 2010 19:210-215.
Annual Meeting Abstracts of the Pharmaceutical Society of Japan, 2001, vol. 121(1), p. 204.
Emergency Medical Service for the treatment of gross hematuria, Treatment Plan Today (Japan) 2002.
Lee et al., Effect of Adenosine Triphosphate in Renal Ischemic Injury: Involvement of NF-kB, Journal of Cellular Physiology 2005 204:792-799.
Li et al., Dehydroarteannuin ameliorates lupus syndrome of BXSB mice by inhibiting production of TNF-alpha and blocking the signalling pathway NK-kappa B translocation, International Immunopharmacology 2006 6:1243-1250.
Mishra et al., Malaria and Acute Kidney Injury, Seminars in Nephrology 2008 28(4):395-408.
Razavi et al., Treatment of Experimental Nephrotic Syndrome with Artesunate, International Journal of Toxicology 2007 26:373-380.
Thanaketpaisarn et al., Artesunate enhances TRAIL-induced apoptosis in human cervical carcinoma cells through inhibition of the NF-kB and PI3K/Akt signalling pathways, International Journal of Oncology 2011 39:279-285.

* cited by examiner

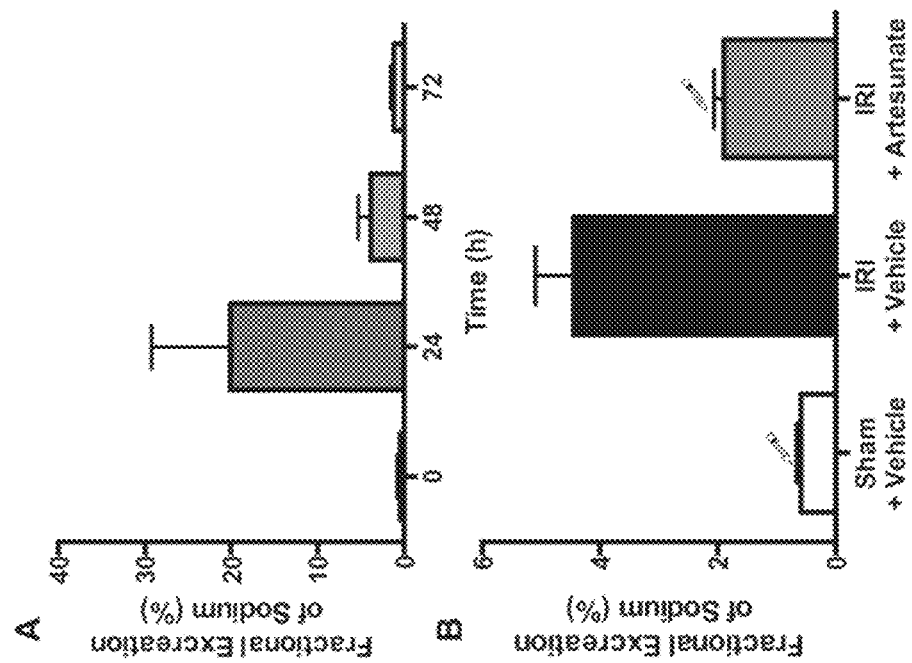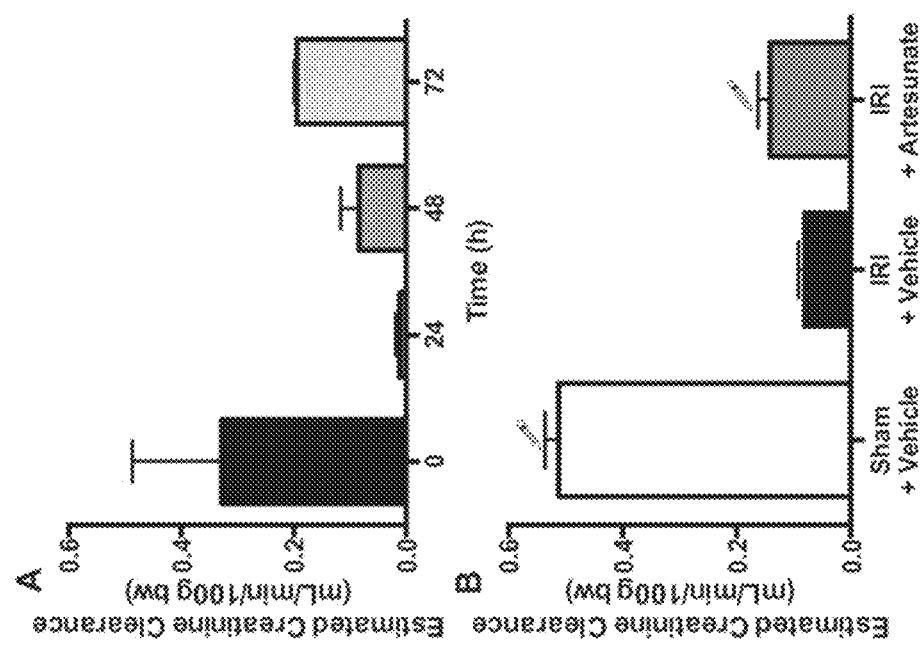

ARTEMISININ AND ITS DERIVATIVES FOR USE IN THE TREATMENT OF KIDNEY DISEASE

CROSS-REFERENCE TO RELATED APPLICATIONS

This application is a 35 U.S.C. §371 national phase application of PCT Application No. PCT/EP2012/075306 filed Dec. 12, 2012, which is hereby incorporated by reference in its entirety.

The present invention relates to the treatment of kidney disease, in particular acute kidney injury, using the anti-malarial compound artemisinin and its derivatives. The present invention also relates to the use of artemisinin and its derivatives in renal surgery and renal transplantation.

Kidney disease includes renal failure (kidney failure) and renal disease in general. Kidney disease refers to a malfunctioning of the kidneys such that the kidneys fail to adequately filter toxins and/or waste products from the blood. The kidney disease can be acute kidney injury or chronic kidney disease.

Acute kidney injury (AKI, also known as acute kidney disease, AKD, and acute renal failure) refers to a rapid loss of kidney function occurring over hours or days. The possible causes are numerous, the most common being a complication of severe infection (sepsis), poor blood flow to the kidneys (seen in dehydration, haemorrhage, cardiac or liver failure, ischaemia/reperfusion injury (IRI) secondary to renal or other organ transplantation or coronary artery bypass graft surgery), toxicity (from nephrotic drugs and radiological contrast), obstruction of the urinary tract (as in malignancy or bladder disease) and due to specific kidney diseases such as nephritis. AKI is diagnosed on the basis of characteristic laboratory findings, such as elevated blood urea nitrogen and/or creatinine, or inability of the kidneys to produce sufficient amounts of urine. AKD is characterised by a rapid loss of the kidney's excretory function and is typically diagnosed by the accumulation of end products of nitrogen metabolism (urea and/or creatinine) or decrease urine output, or both.

AKI is a common complication in hospital patients and is very common in critically ill patients. Studies have estimated mortality resulting from AKI to be in region of 44 to 53%. Despite its prevalence, there is no specific treatment for AKI and many existing interventions rely on management of established disease. Early diagnosis can assist in mitigating the adverse effects of AKI, but renal transplantation therapy may still be required. AKI may lead to a number of complications, including metabolic acidosis, high potassium levels, uraemia, changes in body fluid balance, and effects to other organ systems. Patients suffering from AKI may also be at a higher risk of chronic kidney disease. Bellomo et al. (2012), *Lancet*, 380:756-766 provides a comprehensive view of AKI.

Interventions aimed at reducing both AKI and the secondary fibrosis may in rare circumstances be given as pre-treatment (prior to AKI) or on reperfusion of the previously ischaemic vascular bed, but interventions that can be given once AKI has occurred and resulting in a significant increase in creatinine are very rare. Thus, many efforts are currently being made to develop biomarkers that aid the early detection of AKI. However, there remains a need in the art for the effective prevention and treatment of AKI that can reduce permanent damage done to the kidney as well as prevent complications associated with AKI even after kidney injury has occurred.

Chronic kidney disease (CKD), also known as chronic renal disease, is a progressive loss in renal function over a period of months or years. The symptoms of worsening kidney function are unspecific, and might include feeling generally unwell and experiencing a reduced appetite. Often, chronic kidney disease is diagnosed as a result of screening of people known to be at risk of kidney problems, such as those with high blood pressure or diabetes and those with a blood relative with chronic kidney disease. Chronic kidney disease may also be identified when it leads to one of its recognized complications, such as cardiovascular disease, anaemia or pericarditis.

Chronic kidney disease is identified by a blood test for creatinine. Higher levels of creatinine indicate a falling glomerular filtration rate and as a result a decreased capability of the kidneys to excrete waste products. Creatinine levels may be normal in the early stages of CKD, and the condition is discovered if urinalysis (testing of a urine sample) shows that the kidney is allowing the loss of protein or red blood cells into the urine. To fully investigate the underlying cause of kidney damage, various forms of medical imaging, blood tests and often renal biopsy (removing a small sample of kidney tissue) are employed to find out if there is a reversible cause for the kidney malfunction. Recent professional guidelines classify the severity of chronic kidney disease in five stages, with stage 1 being the mildest and usually causing few symptoms and stage 5 being a severe illness with poor life expectancy if untreated. Stage 5 CKD is also called established chronic kidney disease and is synonymous with the now outdated terms end-stage renal disease (ESRD), chronic kidney failure (CKF) or chronic renal failure (CRF).

To date, there is no specific treatment shown to slow the worsening of chronic kidney disease. If there is an underlying cause to CKD, such as vasculitis, this may be treated directly with treatments aimed to slow the damage. In more advanced stages, treatments may be required for anaemia and bone disease. Severe CKD requires one of the forms of renal replacement therapy; this may be a form of dialysis, but ideally constitutes a kidney transplant.

Artesunate is an anti-malarial drug and is a derivative of artemisinin (also known as qinghaosu), a compound originally isolated from the Chinese herb *Artemisia annua* L. This family of compounds are sesquiterpene lactones, and although artesunate is known to result in adverse side effects (such as bradycardia, electrogram abnormalities, gastrointestinal disturbances and fever), its use in combination with other pharmacologically active agents for the treatment of *falciparum* malaria is standard.

US 2011/0077258 describes the treatment of malaria using artemisinin derivatives in combination with an adjuvant that promotes vasodilation. US 2008/0139642 describes artemisinin derivatives and their preparation and use in immunosuppression. WO 2010/110747 describes the use of artemisinin derivatives for the treatment of asthma and chronic obstructive pulmonary disease (COPD). US 2010/0137246 relates to anti-inflammatory compositions that modulate one or more of Toll-like receptors, Src family kinases, NF-κB molecules, proteases or proteasomes.

Sun et al. (2007), *Zhongguo Zhong Yao Za Zhi*, 32(15): 1547-51 describe the effect of artemisinin pre-treatment on ischemia/reperfusion injury of isolated rat myocardium. Wang et al. (2011), *Invest Ophthalmol Vis Sci*, 52(2):916-9 describe the effect of artesunate on endotoxin-induced uveitis in rats. Li et al. (2008), *Int Immunopharmacol*, 8(3):379-89 describe the ability of artesunate to protect sepsis model mice against heat-killed *E. coli* challenge by decreasing TLR4, TLR9 mRNA expressions and transcription factor NF-κB activation.

The present inventors have surprisingly found that administration of artesunate and its related compounds can provide protection against kidney disease, including acute kidney injury, and even more surprisingly have found that it effect in the treatment of acute kidney injury after diagnosis post, for example, coronary artery bypass surgery (or any other cause of AKI). To date, no specific drug-based intervention has been consistently and reproducibly shown to be protective, making the present findings even more surprising and useful.

Accordingly, in a first aspect of the invention there is provided a compound according to Formula I

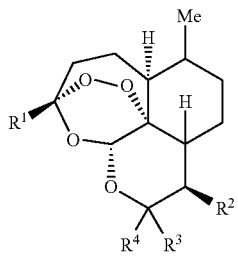

wherein $R^1$ and $R^2$ are independently H or an optionally substituted group selected from an alkyl, a heteroalkyl, an aryl, a heteroaryl, an arylalkyl, and a heteroarylalkyl, and $R^3$ and $R^4$ taken together form a carbonyl (=O); or wherein $R^1$ and $R^2$ are independently H or an optionally substituted group selected from an alkyl, a heteroalkyl, an aryl, a heteroaryl, an arylalkyl, and a heteroarylalkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof for use in the treatment of kidney disease. This aspect of the invention also extends to artemisinin and derivatives thereof, or a pharmaceutically acceptable salt or ester thereof, for us in the treatment of kidney disease. This aspect of the invention also extends to methods of treating kidney disease by administering a compound of Formula I, or a pharmaceutically acceptable salt or ester thereof, to a patient in need thereof. References to a compound of Formula I throughout include pharmaceutically acceptable salts or esters therefore, unless the context requires otherwise.

Kidney disease refers to a malfunctioning of the kidneys such that the kidneys fail to adequately filter toxins and/or waste products from the blood. References to "kidney disease" throughout include acute kidney injury, chronic kidney disease, kidney failure and/or uraemia. Acute kidney injury includes hepatorenal syndrome, a form of acute kidney injury associated with liver disease, rhabdomylosis-associated acute kidney injury and cardiorenal syndrome-induced AKI, as well as AKI caused by other conditions.

The Acute Dialysis Quality Initiative (ADQI) has devised a consensus definition of AKI, as described in Bellomo et al. (2004), *Critical Care*, 8(4):R204-R212. The authors found that AKI can be diagnosed by changes in serum creatinine (increase), urine output (decrease), or both, and these are the stand diagnostic analytes. Physiological markers of renal function include serum creatinine, creatinine clearance, blood urea nitrogen (all specific for the glomerular filtration rate, GFR), angiography, blood oxygenation level dependent MRI, ultrasound (all specific for renal blood flow), urine output, input-output function, urinalysis, osmolality and urine to plasma ratio of creatinine (all specific for tubular function).

AKI may have an obvious and immediate cause, for example burns injury, septic shock, trauma with haemorrhagic shock, diarrhoea, cardiac or renal surgery, although obstruction may also be a cause. AKI may be secondary to other conditions, such as vasculitis, glomerulonephritis and interstitial nephritis. Those most common causes a complication of severe infection (sepsis), poor blood flow to the kidneys (seen in dehydration, haemorrhage, cardiac or liver failure, ischaemia/reperfusion injury (IRI) secondary to renal or other organ transplantation or coronary artery bypass graft surgery), toxicity (from nephrotic drugs and radiological contrast) or obstruction of the urinary tract (as in malignancy or bladder disease). Specific kidney diseases such as nephritis may also be a cause. It is estimated that 30% of patients undergoing major surgery and particularly coronary artery bypass graft surgery experience acute renal injury. Accordingly, references to AKI include AKI induced by such causes, for example burns injury-induced AKI or trauma haemorrhage-induced AKI.

Renal replacement therapy is commonly used to treat kidney disease and can include haemodialysis, peritoneal dialysis, hemofiltration and renal transplantation.

In one embodiment of the invention, in the compound according to Formula I, $R^1$ and $R^2$ are independently H or an optionally substituted $C_1$-$C_{10}$ alkyl and $R^3$ and $R^4$ taken together form a carbonyl (=O) group; or $R^1$ and $R^2$ are independently H or an optionally substituted $C_1$-$C_{10}$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In another embodiment of the invention, in the compound according to Formula I, $R^1$ and $R^2$ are independently H or an optionally substituted $C_1$-$C_{10}$ alkyl, and $R^3$ and $R^4$ taken together form a carbonyl (=O) group, or a pharmaceutically acceptable salt or ester thereof.

In another embodiment of the invention, in the compound according to Formula I, $R^1$ and $R^2$ are independently H or an optionally substituted $C_1$-$C_{10}$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are independently H or an optionally substituted $C_1$-$C_3$ alkyl, and $R^3$ and $R^4$ taken together form a carbonyl (=O) group; or $R^1$ and $R^2$ are independently H or an optionally substituted $C_1$-$C_3$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are independently H or an optionally substituted methyl, and $R^3$ and $R^4$ taken together form a carbonyl (=O) group; or $R^1$ and $R^2$ are independently H or an optionally substituted methyl, $R^3$ is H and $R^4$ is —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are both independently methyl (—CH$_3$), and R$^3$ and R$^4$ taken together form a carbonyl (=O) group; or R$^1$ and R$^2$ are both methyl, R$^3$ is H and R$^4$ is —OR$^5$, wherein R$^5$ is H or an optionally substituted group selected from an alkyl, an aryl, a heteroalkyl, a heteroaryl, an arylalkyl, and a heteroarylalkyl; or a pharmaceutically acceptable salt or ester thereof.

In a further embodiment of the invention, in the compound according to Formula I, R$^1$ and R$^2$ are both an optionally substituted methyl, and R$^3$ and R$^4$ taken together form a carbonyl (=O) group; or R$^1$ and R$^2$ are both methyl, R$^3$ is H and R$^4$ is —OR$^5$, wherein R$^5$ is selected from the group consisting of H, —CH$_3$, —CH$_2$CH$_3$, —CO(CH$_2$)$_2$COOH and —CH$_2$C$_6$H$_4$COOH.

In some embodiments, R$^5$ is H, an alkyl, or an arylalkyl, wherein the alkyl and/or arylalkyl is/are optionally substituted with one more or more of halo, =O, COOR$^6$, OR$^6$ and OCOR$^6$, wherein R$^6$ is H or a C$_1$-C$_6$ alkyl. For example, in one embodiment of the invention, in the compound according to Formula I, R$^1$ and R$^2$ are both a methyl, and R$^3$ and R$^4$ taken together form a carbonyl (=O) group; or R$^1$ and R$^2$ are both methyl, R$^3$ is H and R$^4$ is —OR$^5$, wherein R$^5$ is H, an alkyl, or an arylalkyl, wherein the alkyl and/or arylalkyl is/are optionally substituted with one more or more of halo, =O, COOR$^6$, OR$^6$ and OCOR$^6$, wherein R$^6$ is H or a C$_1$-C$_6$ alkyl.

In some embodiments of the invention, R$^5$ may be selected from the group consisting of H, —CH$_3$, —CH$_2$CH$_3$, —CO(CH$_2$)$_2$COOH and —CH$_2$C$_6$H$_4$COOH.

In some embodiments R$^5$ comprises a carboxyl and optionally the compounds of Formula I are used as salts or esters of the carboxylic acid. In some embodiments, the ester is a simple alkyl ester such as a C$_1$-C$_6$ alkyl ester, where the C$_1$-C$_6$ alkyl is optionally substituted with one or more halo, hydroxyl, or C$_1$-C$_4$ alkoxy groups. Where the compound of Formula I is an ester, it is sometimes a methyl or ethyl or propyl or butyl ester, or a 2-methoxyethyl ester or an ethylene glycol ester.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as C$_{1-10}$. When heteroatoms (N, O and S, for example) replace carbon atoms as in heteroalkyl groups, for example, the numbers describing the group, though still written as e.g. C$_1$-C$_6$, represent the sum of the number of carbon atoms in the group plus the number of such heteroatoms that are included as replacements for carbon atoms in the ring or chain being described.

In some embodiments, the alkyl, alkenyl and alkynyl groups of the invention are C$_1$-C$_{10}$ (alkyl) or C$_2$-C$_{10}$ (alkenyl or alkynyl). Alternatively, they are C$_1$-C$_8$ (alkyl) or C$_2$-C$_8$ (alkenyl or alkynyl). Sometimes they are C$_1$-C$_4$ (alkyl) or C$_2$-C$_4$ (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Typical optional substituents on an alkyl, alkenyl or alkynyl group include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OCOR, COR, and NO$_2$, wherein each R is independently H, C$_1$-C$_8$ alkyl, C$_2$-C$_8$ heteroalkyl, C$_1$-C$_8$ acyl, C$_2$-C$_8$ heteroacyl, C$_2$-C$_8$ alkenyl, C$_2$-C$_8$ heteroalkenyl, C$_2$-C$_8$ alkynyl, C$_2$-C$_8$ heteroalkynyl, C$_6$-C$_{10}$ aryl, or C$_5$-C$_{10}$ heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C$_1$-C$_8$ alkyl, C2-C8 heteroalkyl, C$_1$-C$_8$ acyl, C$_2$-C$_8$ heteroacyl, C$_6$-C$_{10}$ aryl or C$_5$-C$_{10}$ heteroaryl. Alkyl, alkenyl and alkynyl groups can also be substituted by C$_1$-C$_8$ acyl, C$_2$-C$_8$ heteroacyl, C$_6$-C$_{10}$ aryl or C$_5$-C$_{10}$ heteroaryl, each of which can be substituted by the substituents that are appropriate for the particular group. In some embodiments, the alkyl, alkenyl or alkynyl groups are substituted with one more or more of halo, =O, COOR$^6$, OR$^6$ and OCOR$^6$, wherein R$^6$ is H or a C$_1$-C$_6$ alkyl.

While "alkyl" as used herein includes cyclo-alkyl and cyclo-alkylalkyl groups, the term "cyclo-alkyl" may be used herein to describe a carbo-cyclic non-aromatic group that is connected via a ring carbon atom (i.e., its open valence for connecting to a molecule is on a ring carbon), and "cyclo-alkylalkyl" may be used to describe a carbocyclic non-aromatic group that is connected to the molecule through an alkylene linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (—C(O)—), and heteroacyl refers to the corresponding groups wherein at least one carbon other than the carbonyl carbon has been replaced by a heteroatom, for example chosen from N, O and S. The other open valence of the carbonyl is available to connect the acyl group or heteroacyl group to a base molecule. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. In some embodiments, they are C$_1$-C$_8$ acyl groups, which include formyl, acetyl, pivaloyl, and benzoyl, and C$_2$-C$_8$ heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms, for example selected from O, S and N. The inclusion of a heteroatom permits aromaticity in 5-membered rings as well as 6-membered rings. Typical heteroaromatic systems include monocyclic C$_5$-C$_6$ aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. In some embodiments, the ring systems contain 5-12 ring member atoms. In some embodiments, the monocyclic heteroaryls may contain 5-6 ring members, and the bicyclic heteroaryls contain 8-10 ring members.

Aryl and heteroaryl moieties may be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OCOR, COR, and $NO_2$, wherein each R is independently H, $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. In some embodiments, they are substituted with one more or more of halo, =O, $COOR^6$, $OR^6$ and $OCOR^6$, wherein $R^6$ is H or a $C_1$-$C_6$ alkyl. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. The linker may be $C_1$-$C_8$ alkyl or a hetero form thereof. These linkers may also include a carbonyl group, thus making them able to provide substituents as an acyl or heteroacyl moiety. An aryl or heteroaryl ring in an arylalkyl group may be substituted with the same substituents described above for aryl groups. An arylalkyl group may include a phenyl ring optionally substituted with the groups defined above for aryl groups and a $C_1$-$C_4$ alkylene that is unsubstituted or is substituted with one or two $C_1$-$C_4$ alkyl groups, where the alkyl groups can optionally cyclize to form a ring such as cyclopropane, dioxolane, or oxacyclopentane. Similarly, a heteroarylalkyl group may include a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl groups, where the alkyl groups can optionally cyclize to form a ring such as cyclopropane, dioxolane, or oxacyclopentane.

Where an arylalkyl group is described as optionally substituted, the substituents may be on either the alkyl portion or on the aryl or heteroaryl portion of the group. The substituents optionally present on the alkyl portion are the same as those described above for alkyl groups generally; the substituents optionally present on the aryl or heteroaryl portion are the same as those described above for aryl groups generally. In some embodiments, the arylalkyl or heteroarylalkyl are substituted with one more or more of halo, =O, $COOR^6$, $OR^6$ and $OCOR^6$, wherein $R^6$ is H or a $C_1$-$C_6$ alkyl.

"Arylalkyl" groups as used herein are hydrocarbyl groups if they are unsubstituted, and are described by the total number of carbon atoms in the ring and alkylene or similar linker. Thus a benzyl group is a $C_7$-arylalkyl group, and phenylethyl is a $C_8$-arylalkyl.

"Alkylene" as used herein refers to a divalent hydrocarbyl group; because it is divalent, it can link two other groups together. Sometimes it refers to —$(CH_2)_n$— where n is 1-8 and suitably n is 1-4, though where specified, an alkylene can also be substituted by other groups, and can be of other lengths. The open valences of an alkylene need not be at opposite ends of a chain. Thus —CH(Me)- and —$C(Me)_2$- are also included within the scope of the term "alkylenes", as are cyclic groups such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R' is alkyl, this alkyl may optionally be substituted by the remaining substituents listed as embodiments for R' where this makes chemical sense, and where this does not undermine the size limit provided for the alkyl per se; e.g., alkyl substituted by alkyl or by alkenyl would simply extend the upper limit of carbon atoms for these embodiments. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described, in some embodiments, the number of substituents permitted on a group is equal to the number of carbon atoms in the group. Where an optional substituent is attached via a double bond, such as a carbonyl oxygen (=O), the group occupies two available valences, so the total number of other substituents that may be included is reduced according to the number of other available valences.

"Halo" as used herein includes fluoro, chloro, bromo and iodo. "Hetero" atoms may be selected from the group consisting of nitrogen, oxygen, sulphur, phosphorus, boron, chlorine, bromine and iodine. Suitable, the heteroatom is selected from the group consisting of nitrogen, oxygen and sulphur.

Exemplary compounds according to Formula I include artesunate, artemisinin, artemether, dihydroartemisinin (also known as DHA or artenimol, and is the active metabolite of the prodrug artesunate and can be administered orally), artelinic acid and artemotil (also known as arteether). The compounds may be in the alpha or beta forms (in reference to the stereoisomerism of $R^3$ and $R^4$).

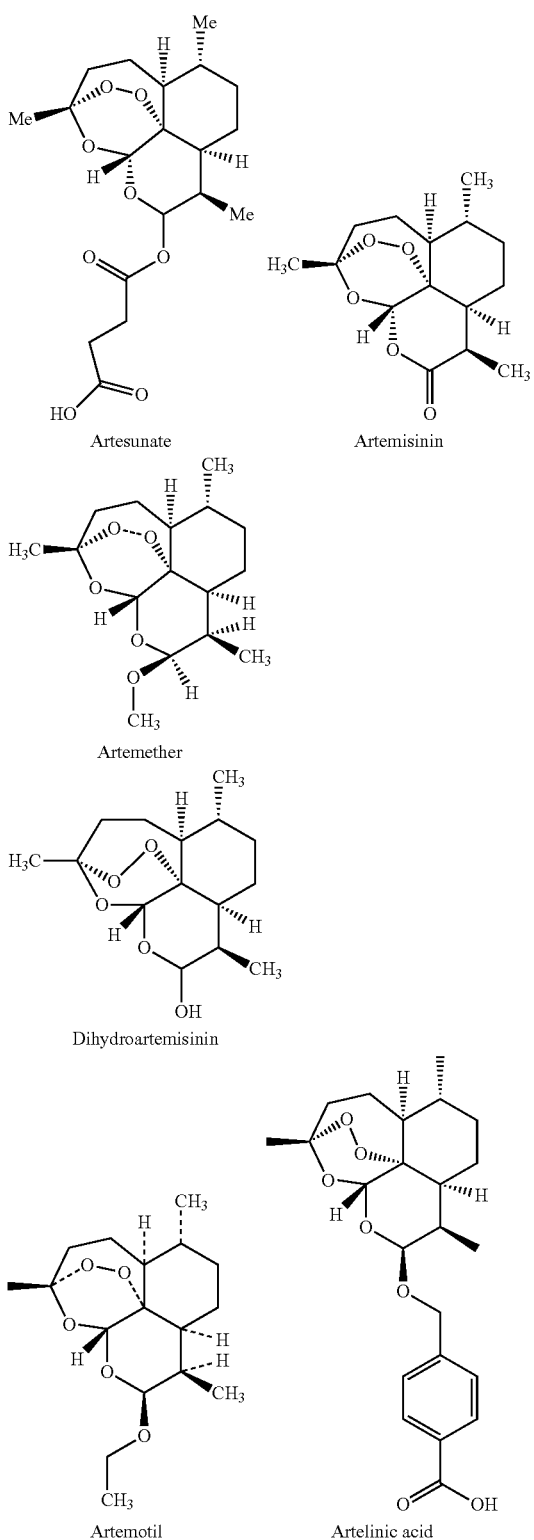

Artesunate

Artemisinin

Artemether

Dihydroartemisinin

Artemotil

Artelinic acid

The systematic (International Union of Pure and Applied Chemistry, IUPAC) name of artemisinin is (3R,5aS,6R,8aS,9R,12S,12aR)-octahydro-3,6,9-trimethyl-3,12-epoxy-12H-pyrano[4,3-j]-1,2-benzodioxepin-10(3H)-one. The systematic (IUPAC) name of dihydroartemisinin is (3R,5aS,6R,8aS,9R,12S,12aR)-decahydro-3,6,9-trimethyl-3,12-epoxy-12H-pyrano[4,3-j]-1,2-benzodioxepin-10-ol. The systematic (IUPAC) name of artelinic acid is 4-[(3R,5aS,6R,8aS,9R,10S,12R,12aR)-decahydro-3,6,9-trimethyl-3,12-epoxy-12H-pyrano[4,3-j]-1,2-benzodioxepin-10-yl]oxy]methylbenzoic acid. For brevity, references to "compounds of Formula I" include the preferred narrower definitions provided above, including the specific compounds disclosed herein (such as artesunate, artemisinin, artemether, dihydroartemisinin, artelinic acid and artemotil).

Accordingly, in one embodiment of the invention there is provided artemisinin or derivatives thereof, or pharmaceutically acceptable salts or esters thereof, for use in the treatment of kidney disease, in particular in the treatment of AKI although also in the treatment of CKD. In one embodiment, the artemisinin derivatives are selected from the group consisting of artesunate, artemether, dihydroartemisinin, artelinic acid and artemotil.

In embodiments of the invention, the compounds of Formula I, or a pharmaceutically acceptable salt or ester thereof, may be provided for use in the treatment of kidney disease.

The compounds used in the present invention can be obtained by any suitable means known to a person of skill in the art. For example, Ro et al. (2006), *Nature,* 440(7086): 940-3 describe the production of the antimalarial precursor artemisinic acid in engineered yeast. Van Herpen et al. (2010), *PLoS One,* 5(12):e14222 describe an engineered form of *Nicotiana benthamiana* that can be used to make artemisinic acid. Alternatively, artemisinin may be obtained from the plant *Artemisia annua* L. (Qinghao) by any suitable means known to a person of skill in the art, for example as described in Kohler et al, (1997), *J Chromatogr A,* 785(1-2):353-60. US2008/0139642 also describes the preparation of artemisinin derivatives.

Artesunate can also be prepared from dihydroartemisinin (DHA, the active metabolite of artemisinin compounds) by reacting it with succinic acid anhydride in basic medium. Pyridine as base/solvent, sodium bicarbonate in chloroform and catalyst DMAP (N,N-dimethylaminopyridine) and triethylamine in 1,2-dichloroethane can be used, with yields of up to 100%. A large scale process may involve treatment of DHA in dichloromethane with a mixture of pyridine, a catalytic amount of DMAP and succinic anhydride. The dichloromethane mixture is stirred for 6-9 h to get artesunate in quantitative yield. The product can be further re-crystallized from dichloromethane. alpha-Artesunate is usually formed (melting point 135-137° C.).

Other means for obtaining artemisinin and its derivatives will be apparent to a person of skill in the art. Artemisinin and derivatives thereof, such as dihydroartemisinin, are also available from suppliers such as Sigma-Aldrich (Poole, Dorset, U.K.).

In embodiments of the invention, a compound of Formula I, or salts or derivatives thereof, may be administered in combination with one or more pharmaceutically active agents.

In a second aspect of the invention there is provided a pharmaceutical composition comprising a compound of Formula I, or salts or ester derivatives thereof, and a pharmaceutically acceptable excipient for use in the treatment of kidney disease. This aspect of the invention also extends to a pharmaceutical composition comprising artemisinin or derivatives thereof and salts thereof, and a pharmaceutically acceptable excipient for use in the treatment of kidney disease. This aspect of the invention also extends to methods of treating kidney disease by administering a pharmaceutical composition of the invention to a patient in need thereof.

Pharmaceutically acceptable excipients include binders, fillers, coatings, disintegrants, solubilisers and solvents.

The compounds of Formula I may be present in the form of a pharmaceutically acceptable salt, for example, hydrochloride (HCl), mesylate, maleate, chloride, bromide, citrate, tartrate, sulphate, phosphate, including any suitable cation (sodium, calcium, benzathine, magnesium, ammonium, zinc, potassium, and so on). Many of the compounds of Formula I may include a carboxylic acid group; for such compounds, a salt can be formed by de-protonation of the carboxylic acid to form a carboxylate.

The pharmaceutical compositions may include one or more further pharmaceutically active agents.

The pharmaceutical compositions may be adapted for administration by any route considered suitable to a person of skill in the art. For example, the pharmaceutical composition may be adapted for oral (including buccal or sublingual), parenteral, intravenous, intramuscular, intrathecal or intraperitoneal administration, or for administration by inhalation. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Dihydroartemisinin (DHA) may be particularly useful for oral administration since it is lipid soluble.

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for administration by inhalation include fine particle dusts or mists which may be generated by means of various types of metered dose pressurised aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Such compositions may be formulated for human or for veterinary medicine. The present applications should be interpreted as applying equally to humans as well as to animals, unless the context clearly implies otherwise.

When preparing any compositions of the invention comprising a compound of Formula I, a person of skill in the art may take any necessary steps to increase the solubility of the compounds of Formula I. For example, the compounds of Formula I may be present in the form of an inclusion complex, such as a cyclodextrin inclusion complex, as described in Ansari et al. (2009), *Arch Pharm Res Vol.*, 32(1):155-65. According, a compound of Formula I may be present in the form of an inclusion complex, for example a cyclodextrin inclusion complex or a hydroxypropyl-β-cyclodextrin complex. Other techniques for increasing the solubility would be apparent to a person of skill in the art, for example the use of surfactants (such as sodium lauryl sulphate) and co-solvents (such as ethanol or DMSO).

Dosages of the pharmaceutical compositions of the present invention can vary between wide limits, depending upon the disease or disorder to be treated, the age and condition of the individual to be treated, etc. and a physician will ultimately determine appropriate dosages to be used. For example, a compound of Formula I, or a pharmaceutically acceptable salt or ester thereof, may be administered in an amount of 0.1 to 50 mg/kg, or 0.1 to 30 mg/kg, or between 0.1 and 3 mg/kg, or between 0.3 and 3 mg/kg. In some embodiments, the artesunate is administered in amount equal to or less than 50, 30, 25, 20, 15, 10, 5 or 1 mg/kg. The compound of Formula I, or a pharmaceutically acceptable salt or ester thereof, may be administered at these dosages only once. Alternatively, a compound of Formula I, or a pharmaceutically acceptable salt or ester thereof, may be administered at these dosages once per day, twice per day, three times per day, four times per day five times per day, wherein preferably each bolus is less than the dosages specified above (rather than a cumulative dosage for the whole day). In some embodiments, the compounds are administered no more than three times per day, or no more than two times per day, or only once per day. In some embodiments, the dosages are given at least 6 hours apart, preferably at least 12 hours apart. The compounds may be administered as a bolus or alternatively may be administered over a period of time as deemed suitable by a skilled person, for example by intravenous drip. In some embodiments, the compounds of Formula I, or pharmaceutically acceptable salts or esters thereof, may be administered in an amount of between 0.1 and 5 mg/kg (or between 0.1 and 3 mg/kg) as a single bolus dose, or once per day, or twice per day, or three times per day, or more.

Importantly, the inventors have surprisingly found that compounds of Formula I (and pharmaceutical compositions of the invention) can be effective in treating acute kidney injury even after symptoms have developed. For example, the present inventors have found that administration 24 hours after AKI (which results in significant increases in serum creatinine) will reduce serum creatinine levels to pre-injury levels and hence shorten recovery time.

Accordingly, in a third aspect of the invention, there is provided a compound for Formula I or a pharmaceutical composition of the invention for use in the treatment of kidney disease, in particular for use in the treatment of AKI, wherein the compound of Formula I (or pharmaceutical composition) is for administration 12 hours after kidney injury. Optionally the compound of Formula I (or pharmaceutical composition) is for administration at least 6, 12, 16, 20, 24, 28, 32, 36, 40, 44, 48, 52, 56, 60, 72 or 96 or more hours after kidney injury episode. For example, the compound of Formula 1 (or pharmaceutical composition) can be for administration after between 6 and 96 hours, 12 and 72, 24 and 72 or 24 and 48 hours after kidney injury. The compound of Formula 1 (or pharmaceutical composition) may be for administration after a maximum of 120 hours after kidney injury, for example after a maximum of 96, 72 or 48 hours after kidney injury.

Alternatively, the compound of Formula I (or pharmaceutical composition) can be for administration at any time after kidney injury, for example any time following diagnosis of AKI by measuring any factors known to be associated with AKI such as serum creatinine, serum urea or urine output.

This aspect of the invention extends to a method of treatment of AKI comprising administering a compound of Formula I or a pharmaceutical composition of the invention to a patient in need thereof, wherein the compound of Formula I is administered at least 6, 12, 16, 20, 24, 28, 32, 36, 40, 44, 48, 52, 56, 60, 72 or 96 or more hours after kidney injury. For example, the compound of Formula 1 (or pharmaceutical composition) can be for administration after between 6 and 96 hours, 12 and 72, 24 and 72 or 24 and 48 hours after kidney injury. The compound of Formula 1 (or pharmaceutical composition) may be for administration after a maximum of 120 hours after kidney injury, for example after a maximum of 96, 72 or 48 hours after kidney injury. Alternatively, the compound of Formula I (or pharmaceutical composition) can be administered at any time after kidney injury, for example any time following diagnosis of AKI by measuring any factors known to be associated with AKI such as serum creatinine, serum urea or urine output.

Therefore, methods of treatment of AKI according to the invention may further comprise a step of diagnosing AKI such as by using any of the known diagnostic markers (for example by measuring serum creatinine and/or urea concentrations, and/or measuring urine output). If AKI is present (or suspected of being present or the patient is deemed to be at risk of developing AKI), then the compound of Formula I (or pharmaceutical composition) is administered as required. In particular, if the levels of creatinine and/or urea are above the expected levels, and/or if urine production or glomerular filtration rate (GFR) is decreased below expected levels, the compound of Formula I (or pharmaceutical composition) is administered to the patient.

The normal or expected levels of serum creatinine, serum urea and urine production would be known to the skilled person for a given patient population and they will be able to determine from these factors (and others) whether or not AKI is present. Bellomo et al. (2004), *Critical Care*, 8(4): R204-R212 describe normal levels and how to determine if AKI is present. For example, increases in serum creatinine of more than 1.5 times, a 25% decrease in glomerular filtration rate (GFR) and/or a level of urine output of less than 0.5 ml/kg/hour over 6 hours suggests the patient is at risk of AKI. Increases in serum creatinine of more than 2 times, a 50% decrease in glomerular filtration rate (GFR) and/or a level of urine output of less than 0.5 ml/kg/hour over 12 hours suggests the patient AKI is present. Increases in serum creatinine of more than 3 times (or a serum creatinine concentration of greater than or equal to 4 mg/dl [350 µmol/l]), a 75% decrease in glomerular filtration rate (GFR) and/or a level of urine output of less than 0.3 ml/kg/hour over 24 hours suggests the patient is suffering from renal failure.

Suitable normal baseline creatinine levels are provided in Table 1.

TABLE 1

Estimated baseline creatinine

| Age (years) | Black males (mg/dl [µmol/l]) | Other males (mg/dl [µmol/l]) | Black females (mg/dl [µmol/l]) | Other females (mg/dl [µmol/l]) |
|---|---|---|---|---|
| 20-24 | 1.5 (133) | 1.3 (115) | 1.2 (106) | 1.0 (88) |
| 25-29 | 1.5 (133) | 1.2 (106) | 1.1 (97) | 1.0 (88) |
| 30-39 | 1.4 (124) | 1.2 (106) | 1.1 (97) | 0.9 (80) |
| 40-54 | 1.3 (115) | 1.1 (97) | 1.0 (88) | 0.9 (80) |
| 55-65 | 1.3 (115) | 1.1 (97) | 1.0 (88) | 0.8 (71) |
| >65 | 1.2 (106) | 1.0 (88) | 0.9 (80) | 0.8 (71) |

Estimated glomerular filtration rate = 75 (ml/min per 1.73 m$^2$) = 186 × (serum creatinine $[S_{Cr}]$) − 1.154 × (age) − 0.203 × (0.742 if female) × (1.210 if black) = exp(5.228 − 1.154 × ln$[S_{Cr}]$) − 0.203 × ln(age) − (0.299 if female) + (0.192 if black).

For example, AKI may be present or the patient may be at risk of AKI if serum creatinine levels are greater than or equal to 1.8 mg/dl (159 µmol) in black males, 1.5 mg/dl (132 µmol) in other males, 1.35 mg/dl (120 µmol) in black females or 1.2 mg/dl (106 µmol/l) in other females.

Accordingly, in one aspect of the invention, methods of treatment include measuring serum creatinine levels and, if they are above normal baseline levels (for example 1.5 times of 2 times or more over the normal expected baseline level) or above the thresholds described above, a compound of Formula I (or pharmaceutical composition of the invention) is administered to the patient.

Kidney injury may be a result of several factors (prerenal or otherwise), for example such as surgery, in particular kidney surgery (such as renal transplantation surgery) and cardiac surgery (such as open heart surgery and coronary artery bypass surgery), trauma-haemorrhage (haemorrhagic shock), sepsis, contrast-induced nephropathy (radio contrast agent-induced AKI), nephrotoxic-drug-induced AKI, hypovolaemia (for example secondary to diarrhoea), ischaemia (for example ischaemia induced by acute occlusion of the renal artery), sepsis, acute heart failure, hepatorenal syndrome, pneumonia (such as pneumonia with septic shock), renal obstruction, inflammatory parenchymal disease, vasculitis, glomerulonephritis, interstitial nephritis, malignant hypertension, pyelonephritis, bilateral cortical necrosis, amyloidosis, malignant disease-induced AKI and albuminuria. Nephrotoxic drugs that can contribute to AKI include inhibitors, radio contrast agents (including iodinated radio contrast agents), aminoglycosides, amphotericin, non-steroidal anti-inflammatory drugs (NSAIDS), β-lactam antibiotics, sulphonamides, acyclovir, methotrexate, cisplatin, cyclosporine, tacrolimus, angiotensin-converting-enzyme inhibitors and angiotensin-receptor blockers. Indeed, one or more of the above causes may be a contributing factor in AKI.

AKI is typically asymptomatic until there is an extreme loss of kidney function, so often it is diagnosed in conjunction with another condition or is diagnosed in at-risk populations, such as those patients undergoing coronary artery bypass graft surgery or renal transplant surgery. Creatinine and urea are the standard diagnostic analytes, although other methods of diagnosis are known to the skilled person. The inventors have surprisingly found that AKI can be treated even after onset of AKI. Therefore, compounds of Formula I and pharmaceutical compositions of the invention are useful not only in the prevention of AKI but also in its treatment following disease onset to aid a speedy recovery and help avoid possible downstream complications.

Generally in embodiments of the invention, the compound of Formula I or the pharmaceutical composition of the invention is for intravenous administration, although other suitable routes of administration would be apparent to the skilled person (as discussed above).

In a fourth aspect of the invention there is provided the use of a compound of Formula I, or a pharmaceutically acceptable salt or ester thereof, in the manufacture of a medicament for the treatment of kidney disease. In another aspect of the invention there is provided the use of artemisinin and derivatives thereof, or a pharmaceutically acceptable salt or ester thereof, for use in the manufacture of a medicament for the treatment of kidney disease. In one embodiment, the artemisinin derivatives are selected from the group consisting of artesunate, artemether, dihydroartemisinin, artelinic acid and artemotil. The compound or pharmaceutical composition may be for administration after diagnosis of acute kidney injury, or after an assessment that deems the patient a risk of developing acute kidney injury. The compound or pharmaceutical composition may alternatively be for administration 12 hours after kidney injury (or indeed at least 6, 12, 16, 20, 24, 28, 32, 36, 40, 44, 48, 52, 56, 60, 72 or 96 or more hours after kidney injury).

In a fifth aspect of the invention there is provided a kit of parts comprising a compound of Formula I, or a pharmaceutically acceptable salt or ester thereof, and one or more further pharmaceutically active agent for simultaneous, separate or sequential administration to a patient in need thereof. The kit of parts may optionally include instructions for use. The compound of Formula I may be present in a unit-dosage form. The kits of parts of the invention are for use in the treatment of kidney disease.

Additional pharmaceutically active compounds include xanthine derivatives (such as pentoxyphylline, for example in a dosage of range of 0.1 to 400 mg/kg), sodium bicarbonate, vitamin D, erythropoietin (for example for administration in the dosage range of 1000 IU/kg), glycyrrhetinic acid derivatives (such as carbenoxolone, for example in the dosage range of 0.01-30 mg/kg) and PPAR-gamma agonists (such as rosiglitazone, pioglitazone, ciglitazone, prostaglandin A1 or prostaglandin D2 (for example in the dosage range of 0.03-10 mg/kg) or 15-deoxyDelta12,14-prostaglandin J2 (15D-PGD2, for example at a dosage range of 0.1-3 mg/kg provided intravenously).

Alternatively, the compounds of Formula I or the pharmaceutical compositions of the invention may be administered alone as the sole pharmaceutically active component or composition used to treat the kidney disease.

The compounds of the first aspect of the invention are also useful in surgical procedures that result in ischaemia-reperfusion of the whole or part of the kidney, kidney transplantation or kidney and pancreas transplantation (and also in coronary artery bypass graft (CABG) surgery), in particular for the perfusion of a kidney during surgery or transplantation to reduce any damage caused in ischaemia. The compounds of the first aspect of the invention may also be useful in renal replacement therapy The invention therefore provides compounds of Formula I for use in such methods.

In embodiments of the invention, the compound of Formula I, or salts or derivatives thereof, may be administered in combination with one or more pharmaceutically active agents. Pharmaceutical compositions of the invention therefore may include one or more further pharmaceutically active agents.

In another aspect of the invention, there is provided the use of a compound of Formula I or the use of a pharmaceutical composition of the invention in a method of kidney transplantation or in a method of CABG surgery. In some embodiments, the compound of Formula I or the pharmaceutical composition of the invention is administered to the patient after completion of the surgery, for example after the donor kidney has been transplanted or after the incision through which the kidney is inserted in closed by, for example, suturing. In particular, the compound or pharmaceutical composition may be administered at least 6, 12, 16, 20, 24, 28, 32, 36, 40, 44, 48, 52, 56, 60, 72 or 96 or more hours after surgery or kidney injury. For example, the compound of Formula 1 (or pharmaceutical composition) can be for administration after between 6 and 96 hours, 12 and 72, 24 and 72 or 24 and 48 hours after surgery or kidney injury. The compound of Formula 1 (or pharmaceutical composition) may be for administration after a maximum of 120 hours after kidney injury, for example after a maximum of 96, 72 or 48 hours after kidney injury.

In the case of renal transplant surgery, the compound of Formula I or pharmaceutical composition of the invention can be administered to the donor patient or the recipient patient, or both. The compound of Formula 1 (or pharmaceutical composition) may be administered to the patient at the above times after ischaemia-reperfusion of the whole or part of the kidney. In some embodiments of the invention, the compound of Formula 1 (or pharmaceutical composition) is for administration to a patient after diagnosis of acute kidney injury or after diagnosis of a risk of acute kidney injury.

In a further aspect of the invention, there is provided a method of kidney transplantation and also a method of CABG surgery comprising administering a compound of Formula I (or a pharmaceutical composition of the invention) to a patient. The compound of Formula 1 (or the pharmaceutical composition) may be administered before, during and/or after surgery. By "after surgery", we mean after completion of the invasive procedure (after the operation), whereas "methods of surgery" in general include post-operative care in which the patient's recovery is monitored, usually in the same hospital or medical facility in which the operation took place In methods where the compound of Formula I or pharmaceutical composition of the invention is administered after surgery, the compound or composition is generally administered 12 or more hours after completion of surgery, for example at least 6, 12, 16, 20, 24, 28, 32, 36, 40, 44, 48, 52, 56, 60, 72 or 96 or more hours after surgery. Generally, the compound of Formula 1 (or pharmaceutical composition) may be for administration after a maximum of 120 hours after surgery (i.e. after the operation), for example after a maximum of 96, 72 or 48 hours after surgery.

In some methods of kidney transplantation or methods of CABG surgery, after surgery (for example after transplant of the donor kidney) is complete, the patient is monitored for AKI, for example by measuring serum creatinine, serum urea and/or urine output, or any other suitable diagnostic markers for AKI. If the patient presents with symptoms of AKI or AKI is diagnosed as being present or the patient is determined to be at risk of developing AKI, then the compound of Formula I or pharmaceutical composition of the invention can be administered to treat the AKI. This avoids problems associated with unnecessary administration of drugs to patients by waiting to assess whether AKI develops post-surgery, or if the patient is at increased risk of developing AKI, rather than having to treat all patients prophylactically.

In methods of the invention, the compound of Formula I (or pharmaceutical composition) is generally administered intravenously.

Methods of kidney transplantation can be any method known to be suitable to the skilled person, such as those described in "Guidelines on Renal Transplantation", Käthle et al., (2006), *European Association of Urology*. Methods of kidney transplantation of the invention include methods of kidney and pancreas transplantation where a pancreas is transplanted at the same time as a kidney. Basic methods of kidney transplantation comprise a step of surgically implanting a donor kidney (from a donor patient) into a recipient patient.

Basic methods of CABG include the steps of taking a blood vessel from another part of the patient's body, usually the chest or leg (for example the internal mammary artery), and attaching it to the coronary artery above and below a narrowed area or blockage in the existing artery. This new blood vessel is known as a graft. The graft diverts the flow of blood around the part of the coronary artery that is narrowed or blocked. Usually, a surgeon will carry out several grafts to make sure the procedure does not have to be repeated in the future. After implantation of the graft vessel, the sternum and incision are closed using sutures. Methods of CABG will be apparent to the skilled person.

In methods of kidney transplantation, the donor kidney may be perfused using a solution comprising a compound of Formula I, and accordingly methods of the invention may include such a step. For example, such a solution may be a reperfusion solution comprising a compound of Formula I, or a pharmaceutically acceptable salt or ester thereof, and one or more volume expanders. In one embodiment, the volume expander is a crystalloid or a colloid, or a combination of a crystalloid and a colloid.

A crystalloid is an aqueous solution of salts comprising at least two ions selected from the group consisting of sodium ions, chloride ions, lactate ions, potassium ions and calcium ions. In some embodiments, the crystalloid is an aqueous solution comprising at least three ions selected from the group consisting of sodium ions, chloride ions, lactate ions, potassium ions and calcium ions. In some embodiments, the crystalloid is an aqueous solution comprising at least four ions selected from the group consisting of sodium ions, chloride ions, lactate ions, potassium ions and calcium ions. In some embodiments, the crystalloid is an aqueous solution comprising sodium ions, chloride ions, lactate ions, potassium ions and calcium ions. The crystalloid may also comprise bicarbonate ions and/or glucose.

Example crystalloids include aqueous solutions of mineral salts (such a saline, Ringer's lactate or Hartmann's solution) or other water-soluble molecules. One liter of Ringer's lactate solution (also known as lactated Ringer's solution or Ringer's Lactate) generally contains:
 about 130 mEq of sodium ions=130 mmol/L
 about 109 mEq of chloride ions=109 mmol/L
 about 28 mEq of lactate=28 mmol/L
 about 4 mEq of potassium ions=4 mmol/L
 about 3 mEq of calcium ions=1.5 mmol/L Generally, the sodium, chloride, potassium and lactate comes from NaCl (sodium chloride), $NaC_3H_5O_3$ (sodium lactate), $CaCl_2$ (calcium chloride), and KCl (potassium chloride). However, it would be apparent to a person of skill in the art that other components could be used to reach the desired ion concentrations. The pH of Ringer's lactate can be in the range of 6 to 7, for example 6.5, although it is generally an alkalizing solution.

One liter of Hartmann's solution (also known as compound sodium lactate) can contain:
 131 mEq of sodium ions=131 mmol/L.
 111 mEq of chloride ions=111 mmol/L.
 29 mEq of lactate=29 mmol/L.
 5 mEq of potassium ions=5 mmol/L.
 4 mEq of calcium ions=2 mmol/L Accordingly, in one embodiment, the reperfusion solution comprises a compound of Formula I, or a pharmaceutically acceptable salt or ester thereof, and a crystalloid volume expander, wherein the crystalloid volume expander is an aqueous solution comprising at least three ions selected from the group consisting of sodium ions, chloride ions, lactate ions, potassium ions and calcium ions. In another embodiment, the reperfusion solution comprises a compound of Formula I, or a pharmaceutically acceptable salt or ester thereof, and a crystalloid volume expander, wherein the crystalloid volume expander is an aqueous solution comprising at least four ions selected from the group consisting of sodium ions, chloride ions, lactate ions, potassium ions and calcium ions. In a further embodiment, the reperfusion solution comprises a compound of Formula I, or a pharmaceutically acceptable salt or ester thereof, and a crystalloid volume expander, wherein the crystalloid volume expander is an aqueous solution comprising sodium ions, chloride ions, lactate ions, potassium ions and calcium ions.

In these embodiments, the ions may be present at any suitable concentration known to the skilled person. For example, the sodium ions may be present in a concentration of about 100 mmol/L to about 150 mmol/L. The chloride ions may be present in a concentration of about 90 mmol/L to about 120 mmol/L. The lactate ions may be present in a concentration of about 20 mmol/L to about 30 mmol/L. The potassium ions may be present in a concentration of about 2 mmol/L to about 6 mmol/L. The calcium ions may be present in a concentration of about 1 mmol/L to 5 about mmol/L. Bicarbonate ions (if present) may be present in a concentration of about 10 mmol/L to about 50 mmol/L. Glucose (if present) may be present at a concentration of about 2% to about 10% by weight, for example about 3% to about 6% by weight.

Accordingly, in another embodiment, the reperfusion solution comprises a compound of Formula I, or a pharmaceutically acceptable salt or ester thereof, in an aqueous solution comprising:
 about 100 mmol/L to about 150 mmol/L of sodium ions
 about 90 mmol/L to about 120 mmol/L of chloride ion
 about 20 mmol/L to about 30 mmol/L of lactate
 about 2 mmol/L to about 6 mmol/L of potassium ions
 about 1 mmol/L to about 5 mmol/L of calcium ions As will be apparent to the skilled person, the above aqueous solution is an example of a suitable crystalloid volume expander.

The reperfusion solution may alternatively include a colloid volume expander, or it may contain a mixture of the crystalloid volume expander described above and a colloid volume expander. Examples of suitable colloids include gelatin, succinylated gelatin, albumin, dextran (for example dextran 40, dextran 70 or dextran 75), blood, or etherified starch (also known as hydroxyethyl starch, tetrastarch, hetastarch or pentastarch). The colloids are generally aqueous solutions comprising these components. For example, the colloid may comprise at least one component selected from the groups consisting of gelatin, succinylated gelatin, albumin, dextran, blood and etherified starch.

Commercially available colloids include Haemaccel® (Piramal, containing degraded gelatin polypeptides crosslinked via urea bridges), Gelofusine® (Braun, succinylated gelatin (modified fluid gelatin, average molecular weight 30 000) 40 g (4%), Na+ 154 mmol, Cl− 120 mmol/liter), Gelopasma® (Fresenius Kabi, partially hydrolysed and succinylated gelatin (modified liquid gelatin) (as anhydrous gelatin) 30 g (3%), $Na^+$ 150 mmol, $K^+$ 5 mmol, $Mg^{2+}$ 1.5 mmol, $Cl^-$ 100 mmol, lactate 30 mmol/liter), Isoplex® (Beacon, succinylated gelatin (modified fluid gelatin, average molecular weight 30 000) 40 g (4%), $Na^+$ 145 mmol, $K^+$ 4 mmol, $Mg^{2+}$ 0.9 mmol, $Cl^-$ 105 mmol, lactate 25 mmol/liter), Volplex® (Beacon, succinylated gelatin (modified fluid gelatin, average molecular weight 30 000) 40 g (4%), $Na^+$154 mmol, $Cl^-$ 125 mmol/liter), Voluven® (Fresenius Kabi, 6% hydroxyethyl starch (weight average molecular weight 130 000) in 0.9% sodium chloride injection), Volulyte® (Fresenius Kabi, 6% hydroxyethyl starch (weight average molecular weight 130 000) in sodium chloride intravenous infusion 0.6%, containing $Na^+$ 137 mmol, $K^+$ 4 mmol, $Mg^{2+}$ 1.5 mmol, $Cl^-$ 110 mmol, acetate 34 mmol/liter), Venofundin® (Braun, 6% hydroxyethyl starch (weight average molecular weight 130 000) in 0.9% sodium chloride injection), Tetraspan® (Braun, hydroxyethyl starch (weight average molecular weight 130 000) 6% or 10% in sodium chloride 0.625%, containing $Na^+$ 140 mmol, $K^+$ 4 mmol, $Mg^{2+}$ 1 mmol, $Cl^-$ 118 mmol, $Ca^{2+}$ 2.5 mmol, acetate 24 mmol, malate 5 mmol/liter), HAES-steril® (Fresenius Kabi, pentastarch (weight average molecular weight 200 000) 10% in sodium chloride intravenous infusion 0.9%), Hemohes® (Braun, 6% or 10% pentastarch (weight average molecular weight 200 000), in sodium chloride intravenous infusion 0.9%), HyperHAES® (Fresenius Kabi, hydroxyethyl starch (weight average molecular weight 200 000) 6% in sodium chloride intravenous infusion 7.2%) and RescueFlow® (Vitaline, dextran 70 intravenous infusion 6% in sodium chloride intravenous infusion 7.5%).

Accordingly, in one embodiment, the reperfusion solution comprises a compound of Formula I, or a pharmaceutically acceptable salt or ester thereof, and a colloid volume expander and/or a crystalloid volume expander, wherein the colloid volume expander comprises one or more components selected from the group consisting of gelatin, succinylated gelatin, albumin, dextran, blood, and etherified starch, and wherein the crystalloid volume expander is an aqueous solution comprising at least three ions selected from the group consisting of sodium ions, chloride ions, lactate ions, potassium ions and calcium ions.

In a further embodiment the reperfusion solution comprises a compound of Formula I, or a pharmaceutically acceptable salt or ester thereof, and a colloid volume expander and/or a crystalloid volume expander, wherein the colloid volume expander comprises one or more components selected from the group consisting of gelatin, succinylated gelatin, albumin, dextran, blood, and etherified starch, and wherein the crystalloid volume expander comprises:
   about 100 to 150 mmol/L of sodium ions
   about 90 to 120 mmol/L of chloride ion
   about 20 to 30 mmol/L of lactate
   about 2 to 6 mmol/L of potassium ions
   about 1 to 5 mmol/L of calcium ions.

The amount of the reperfusion solution provided to an organ can be determined by a person of skill in the art.

The reperfusion solutions are aqueous solutions. The concentrations of each of the components can be determined by a person of skill in the art according to requirements. For example, the concentration of a compound of Formula I (or a pharmaceutically acceptable salt or ester thereof) may be $10^{-6}$M to $10^{-2}$M, for example $10^{-5}$M to $3\times10^{-3}$M. In some embodiments, the compound for Formula I (or a pharmaceutically acceptable salt or ester thereof) is present at a concentration equal to or less than $10^{-2}$M. In some embodiments, the compound for Formula I (or a pharmaceutically acceptable salt or ester thereof) is present at a concentration of equal to or greater than $10^{-6}$M or $10^{-5}$M.

The reperfusion solutions may be hypotonic, hypertonic or isotonic. In some embodiments, the volume expander (and/or reperfusion solution) is an isotonic aqueous solution.

The reperfusion solutions may include additional components as deemed suitable by a person of skill in the art. For example, the reperfusion solution may also contain one or more additional components selected from the group consisting of mannitol, haemoglobin (for example in a dosage range of 2 to 9 g/liter), pegylated haemoglobin (for example MP4OX® (4 g/L PEG-Hb in lactated electrolyte solution, Sangart)), pegylated carboxyhaemoglobin (for example MP4CO® (43 mg/mL pegylated carboxyhaemoglobin [≥90% CO haemoglobin saturation] in physiological acetate electrolyte solution, Sangart)), platelets (for example in a dosage of equal to or more than $50\times10^8$/liter), fibrinogen (for example in a dosage of 50 mg/kg), antifibrinolytic agents, recombinant activated coagulation factor VII (rFVIIa) and pro-thrombin complexes.

When preparing aqueous solutions comprising a compound of Formula I, a person of skill in the art may take any necessary steps to increase the solubility of the compounds of Formula I. For example, the compounds of Formula I may be present in the form of an inclusion complex, such as a cyclodextrin inclusion complex, as described in Ansari et al. (2009), *Arch Pharm Res Vol.*, 32(1):155-65. According, a compound of Formula I may be present in the form of an inclusion complex, for example a cyclodextrin inclusion complex or a hydroxypropyl-β-cyclodextrin complex. Other techniques for increasing the solubility would be apparent to a person of skill in the art, for example the use of surfactants (such as sodium lauryl sulphate) and co-solvents (such as ethanol or DMSO).

Methods of kidney transplantation of the invention may include removal of a diseased kidney or kidneys. Alternatively, the diseased kidneys may remain in the recipient patient.

Methods of kidney transplantation described herein include partial kidney transplantation as well as whole kidney transplantation.

In a still further aspect of the invention, there is provided a method of perfusing a kidney comprising bathing the kidney in a solution (for example a reperfusion solution as discussed above) comprising a compound of Formula I. The method is conducted ex vivo. The kidney is obtained from a donor patient (either a live patient or a cadaver). Accordingly, there is also provided a method of kidney transplantation wherein the donor kidney is perfused according to the method of perfusion of the invention. The perfusion of the kidney occurs prior to, during and/or after implantation into the donor patient.

In a further aspect of the invention there is also provided a compound according to Formula I, or a pharmaceutically acceptable salt or ester thereof, or a pharmaceutical composition of the invention, for use in the treatment of uraemia. Uraemia refers to the retention of urea and other waste products in the blood. Uraemia may be the result of kidney disease, although could also be the result of other factors, for example increased production of urea in the liver (due to, for example, a high protein diet or gastrointestinal bleeding), decrease elimination of urea (due to, for example, decreased blood flow through the kidneys due to cardiac arrest or hypotension, or bladder rupture), dehydration or kidney infection. However, generally this aspect of the invention relates to kidney disease-associated uraemia (for example AKI-associated uraemia). This aspect of the invention also extends to methods of treating uraemia by administering a compound of Formula I, or a pharmaceutically acceptable salt or ester thereof, or a pharmaceutical composition of the invention, to a patient in need thereof In another aspect of the invention, there is provided a dialysate comprising a compound of Formula I, or a pharmaceutically acceptable salt or ester thereof. In a further aspect of the invention, there is provided a compound of Formula I, or a pharmaceutically acceptable salt or ester thereof, for use in dialysis. This aspect of the invention also extends to the use of a compound of Formula I, or a pharmaceutically acceptable salt or ester thereof, in the manufacture of a dialysate.

Dialysates (also known as dialysis solutions) are solutions used in kidney dialysis. Dialysates flow on the opposite side of a semi-permeable membrane to the blood being filtered. Dialysates are generally aqueous solutions and may contain ions such as sodium, chloride, lactate and bicarbonate. The solution may also contain glucose or a dextrin, such as icodextrin, or similar compounds. Icodextrin is a starch-derived, branched water soluble glucose polymer (by α-(1→4) and less than 10% α-(1→6) glycosidic bonds, making it a type of dextrin, with a weight-average molecular weight of between 13,000 and 19,000 Daltons and a number-average molecular weight between 5,000 and 6,500 Daltons) used as colloid osmotic agent in the form of an aqueous solution. Other ions that may be present include calcium and magnesium ions, although generally at lower concentrations that sodium, chloride, lactate and bicarbonate ions.

There are several types of dialysis, although generally the dialysate of the invention will be used in haemodialysis or peritoneal dialysis.

Example commercially available dialysates include Extraneal® (Baxter, an icodextrin-containing dialysate), Gambrisol Trio® (Gambro, a glucose-containing dialysate) and Physioneal® (Baxter, a glucose-containing dialysate)

As an example, Extraneal® (icodextrin) is a peritoneal dialysis solution containing the colloid osmotic agent icodextrin. Icodextrin is a starch-derived, water-soluble glucose polymer linked by alpha (1-4) and less than 10% alpha (1-6) glucosidic bonds with a weight-average molecular weight between 13,000 and 19,000 Daltons and a number average molecular weight between 5,000 and 6,500 Daltons. Each 100 mL of Extraneal contains icodextrin (7.5 g), sodium chloride (535 mg), sodium lactate (448 mg), calcium chloride (25.7 mg), magnesium chloride (5.08 mg). The electrolyte content per liter accordingly is:

Sodium: 132 mEq/L
Calcium: 3.5 mEq/L
Magnesium: 0.5 mEq/L
Chloride: 96 mEq/L
Lactate: 40 mEq/L Accordingly, in some embodiments of the invention, the dialysate may further comprise, in addition to a compound of Formula I, at least two ions selected from the group consisting of sodium, chloride, lactate and bicarbonate. In some embodiments of the invention, the dialysate may comprise, in addition to a compound of Formula I, at least three ions selected from the group consisting of sodium, chloride, lactate and bicarbonate. In another embodiment of the invention, the dialysate may comprise sodium, chloride, lactate and bicarbonate ions, in addition to a compound of Formula I.

In further embodiments of the invention, the dialysate may further comprise calcium and/or magnesium ions. In some embodiments, the calcium and magnesium ions, if present, are present in a concentration less than each of the sodium, chloride, lactate and bicarbonate ions.

In some embodiments of the invention, the dialysate may comprise an osmotic agent. Example osmotic agents include glucose, polyglucose or amino acids. Polyglucose dialysates are discussed in Grzegorzewska et al. (2001), Adv Perit Dial, 17:101-8. The amino acids may be essential or non-essential amino acids and may be in the L- or D-isoforms. In some embodiments of the invention, the dialysate may comprise at least one component selected from the group consisting of glucose, polyglucose, an amino acid, icodextrin and bicarbonate ions. For example, the dialysate may comprise a compound of Formula I, or a pharmaceutically acceptable salt or ester thereof, at least two ions selected from the group consisting of sodium, chloride and lactate ions, and at least one component selected from the group consisting of glucose, polyglucose, amino acids, icodextrin and bicarbonate.

Sodium ions may be present in a concentration of about 100 mEq/L to about 150 mEq/L. Chloride ions may be present an amount of about 75 mEq/L to about 125 mEq/L. Lactate ions may be present in an amount of about 10 mEq/L to about 50 mEq/L. Bicarbonate ions may be present in an amount of about 10 mEq/L to about 50 mEq/L. Calcium ions may be present in an amount of less than 5 mEq/L, for example from about 1 mEq/L to about 5 mEq/L. Magnesium ions may be present in an amount of less than 5 mEq/L, for example from about 0.1 mEq/L to about 2 mEq/L.

Icodextrin may be present in an amount of about 50 g/L to 100 g/L. Glucose may be present in an amount of about 5 g/L to about 50 g/L.

The compound of Formula 1 may be present in a concentration that provides protection to the kidney from damage during dialysis or during kidney disease. For example, a compound of Formula I, or a pharmaceutically acceptable salt or ester thereof, may be present in an amount of 10-6M to 10-2M, for example 10-5M to 3×10-3M. In some embodiments, the compound for Formula I (or a pharmaceutically acceptable salt or ester thereof) is present at a concentration equal to or less than 10-2M. In some embodiments, the compound for Formula I (or a pharmaceutically acceptable salt or ester thereof) is present at a concentration of equal to or greater than 10-6M or 10-5M.

In one embodiment of the invention there is provided artesunate for use in the treatment of acute kidney injury. The artesunate is for intravenous administration and may be administered 12 hours or more after kidney injury (or after AKI diagnosis). Methods of treatment of AKI include administering artesunate in an amount of between 0.1 and 3 mg/kg intravenously to a patient in need thereof. Methods of kidney transplantation include administering artesunate to the donor patient prior to, during and/or after surgery to minimise the risk of kidney disease. Alternatively, the method of kidney transplantation may comprise measuring serum creatinine levels post-surgery and administered artesunate should the patient develop AKI or be deemed to be at risk of developing AKI.

Features of the first aspect of the invention apply to the second and subsequent aspects of the invention, mutatis mutandis.

The invention will now be described with reference to the following Examples, which are presented for the purposes of reference only and are not intended to be limiting on the scope of the invention. In the Examples, references are made to a number of Figures, in which:

FIG. 1 shows alterations in MAP in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. ★ $P<0.05$ sham vs. HS Control.

FIGS. 2A, 2B, and 2C show alterations in serum levels of (a) urea and (b) creatinine; and (c) creatinine clearance, in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. ★ $P<0.05$ vs. HS Control.

FIGS. 3A, 3B, and 3C show alterations in serum levels of (a) AST, (b) ALT and (c) CK in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. ★ $P<0.05$ vs. HS Control.

FIGS. 6A, 6B, 6C, and 6D show the effect of 30 min ischemia followed by different lengths of reperfusion (24, 48 or 72 h) on glomerular and tubular function. Serum urea (A), serum creatinine (B) and estimated creatinine clearance (C) were measured as indicators of glomerular function, and fractional excretion of sodium (D) as an indicator of tubular function (in different sets of animals for each time point). The peak of dysfunction in all parameters occurs 24 h after the onset of reperfusion. Pre-ischemia: n=4; 24 h reperfusion: n=4; 48 h reperfusion: n=8; 72 h reperfusion: n=4. Data are presented as mean±s.e.m. of n observations, ★★ $P<0.0001$ vs. pre-ischemia, ★ $P<0.001$ vs. pre-ischemia.

FIGS. 7A, 7B, 7C, 7D, and 7E show the effect of 30 min ischemia followed by different lengths of reperfusion (24, 48 or 72 h) on renal injury. Representative histological H&E images of rat renal tissue were taken from groups without renal ischemia (pre-ischemia, A), or from rats subjected to 30 min of renal ischaemia followed by reperfusion for 24 h (B), 48 h (C) or 72 h (D). Ten randomly selected fields from three individual kidneys (n=3) per group were selected and analysed (total fields=30) for the determination of percentage background white space using ImageJ software and represented as tissue surface area per field (E). Data are presented as mean±s.e.m. of n observations, ★ $P<0.05$ vs. pre-ischemia.

Figure 8:
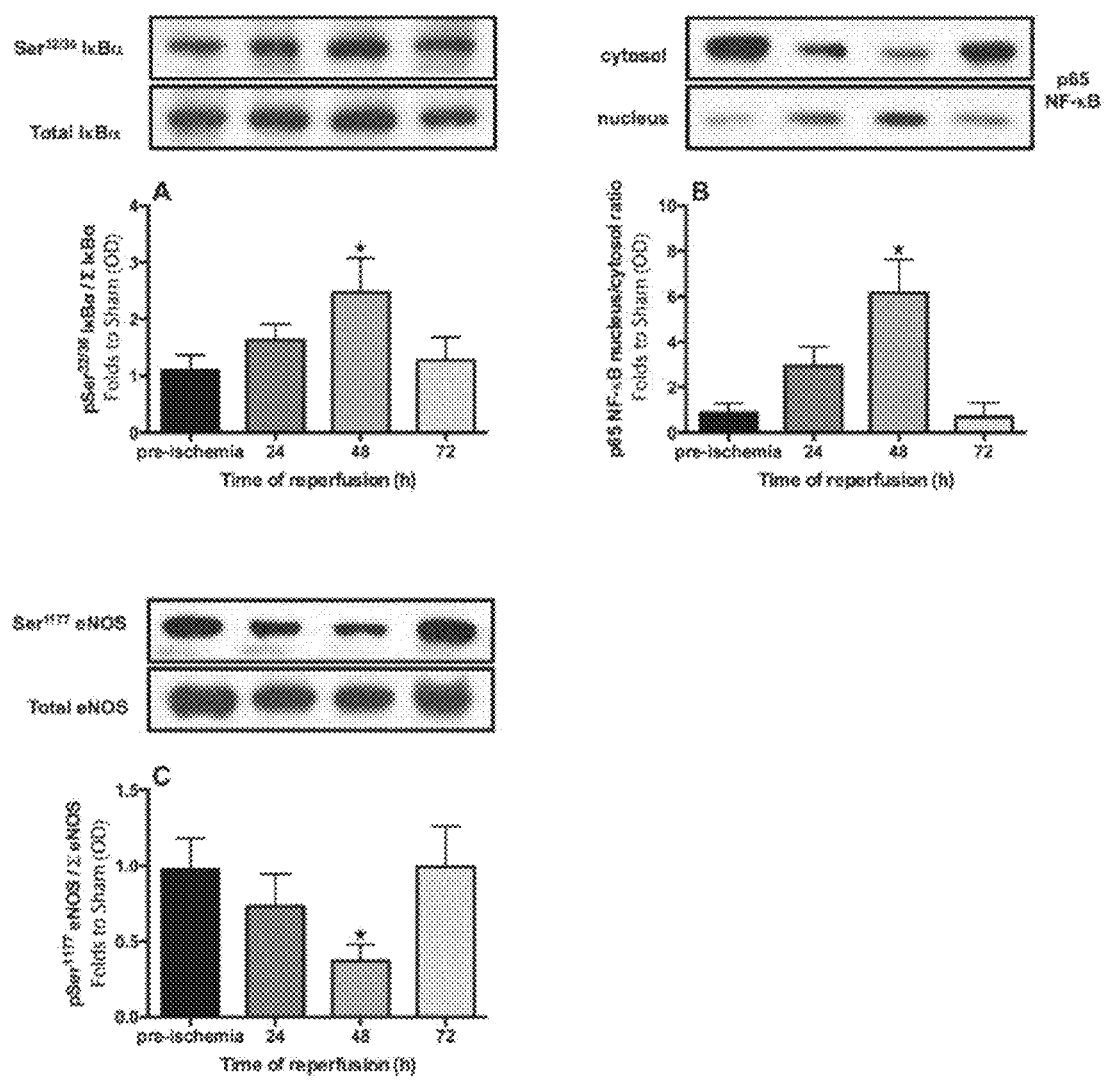

FIGS. 8A, 8B, and 8C show the effect of 30 min ischemia followed by different length of reperfusion (24, 48 or 72 h) on the activation of IκBα, NF-κB and endothelial nitric oxide synthase (eNOS). Activation of IκBα (A) was measured as phosphorylation of Ser32/36 on IκBα during the course of reperfusion. The activation of IκBα results in nuclear translocation of the p65 subunit of NF-κB (B). The activation of eNOS (C) was measured as phosphorylation of Ser1177 during the course of reperfusion. Data are presented as mean±s.e.m. of n observations, ★ $P<0.05$ vs. pre-ischemia.

FIGS. 9A, 9B, 9C, and 9D show serum urea (A) and creatinine levels (B) measurements, from rats, as biochemical markers of renal dysfunction over the course of reperfusion (n=4). Serum urea (C) and creatinine levels (D) were measured at the end of 48 h of reperfusion subsequent to either sham-operation (Sham+Vehicle, n=8) or renal ischaemia/reperfusion (IRI+Vehicle, n=8; IRI+Artesunate 0.3 mg/kg i.v., n=7). Vehicle or artesunate were administered 24 h after the onset of reperfusion, i.e. the peak of dysfunction (see A & B). Data represent mean±SEM for n observations. Data were analysed by a one-way ANOVA followed by a Dunnett's test for comparison of the sham/treated groups with IRI+Vehicle group; ★ $P<0.05$ vs. IRI+Vehicle.

FIGS. 10A and 10B show creatinine clearance (A) measurements, from rats, as a biochemical marker of glomerular dysfunction over the course of reperfusion (n=4). Estimated creatinine clearance (B) was measured at the end of 48 h of reperfusion subsequent to either sham-operation (Sham+Vehicle, n=8) or renal ischaemia/reperfusion (IRI+Vehicle, n=8; IRI+Artesunate 0.3 mg/kg i.v., n=7). Vehicle or artesunate were administered 24 h after the onset of reperfusion, i.e. the peak of dysfunction (see A). Data represent mean±SEM for n observations. Data were analysed by a one-way ANOVA followed by a Dunnett's test for comparison of the sham/treated groups with IRI+Vehicle group; ★ $P<0.05$ vs. IRI+Vehicle.

FIGS. 11A and 11B show fractional excretion of sodium (A), which was repeatedly measured, from rats, as a biochemical marker of tubular dysfunction over the course of reperfusion (n=4). Fractional excretion of sodium (B) was measured at the end of 48 h of reperfusion subsequent to either sham-operation (Sham+Vehicle, n=8) or renal ischaemia/reperfusion (IRI+Vehicle, n=8; or IRI+Artesunate 0.3 mg/kg i.v., n=7). Vehicle or artesunate were administered 24 h after the onset of reperfusion, i.e. the peak of dysfunction (see A). Data represent mean±SEM for n observations. Data were analysed by a one-way ANOVA followed by a Dunnett's test for comparison of the sham/treated groups with IRI+Vehicle group; ★ $P<0.05$ vs. IRI+Vehicle.

EXAMPLES

The animal protocols followed in this study were approved by the local Animal Use and Care Committee in accordance with the derivatives of both the Home Office Guidance on the Operation of Animals (Scientific Procedures) Act 1986 published by Her Majesty's Stationary Office and the Guide for the Care and Use of Laboratory Animals of the National Research Council.

1. Evaluation of the Effects of Artesunate on Organ Injury and Dysfunction Induced by Trauma Haemorrhage in the Rat 1.1 Surgical Procedure Thirty-five male Wistar rats (271±5 g) were anaesthetised with sodium thiopentone (120 mg/kg i.p., LINK Pharmaceuticals Ltd., West Sussex, UK) and anaesthesia was maintained by supplementary injections (~10 mg/kg i.v.) of sodium thiopentone as and when required. The animals were placed onto a thermostatically controlled heating mat (Harvard Apparatus Ltd., Kent, UK) and body temperature was maintained at 37±1° C. by means of a rectal probe attached to a homeothermic blanket. A tracheotomy was performed by inserting into the lumen of the trachea a small length of polyethylene tubing [Internal Diameter (ID) 1.67 mm, Portex, Kent, UK] to maintain airway patency and facilitate spontaneous respiration. The left femoral artery was cannulated (ID 0.40 mm, Portex) and connected to a pressure transducer (SP844 blood pressure sensor, Memscap, U.S.A.) for the measurement of mean arterial blood pressure (MAP) and derivation of heart rate (HR) from the pulse waveform, which were both displayed on a data acquisition system (Powerlab 8SP, Chart v5.5.3, AD Instruments, Hastings, U.K.) installed on an Intel-based computer running Windows XP for the duration of the experiment. The right carotid artery was cannulated (ID 0.58 mm, Portex) to facilitate the withdrawal of blood using a heparinised syringe. The right jugular vein was cannulated (ID 0.40 mm, Portex) for the administration of Ringer's Lactate (RL), shed blood, test compounds and/or vehicle. The bladder was also cannulated (ID 0.76 mm, Portex) for the collection of urine. Upon completion of the surgical procedure, cardiovascular parameters were allowed to stabilise for a period of 15 min.

1.2 Haemorrhage and Resuscitation

After the stabilisation period, blood was withdrawn via the cannula inserted in the right carotid artery in order to achieve a fall in MAP to 35±5 mmHg within 10 min. From this point onwards, MAP was maintained at 35±5 mmHg for a period of 90 min either by further withdrawal of blood during the compensation phase (MAP rises following blood withdrawal due to sympathetic response) or administration of Ringer's Lactate i.v. during the decompensation phase (animals are unable to increase and maintain high MAP). The average volume of blood withdrawn during haemorrhage was 9.8±0.2 ml (n=31, across all haemorrhaged groups). At 90 min after initiation of haemorrhage, resuscitation was performed with 20 ml/kg Ringer's Lactate i.v. over a period of 10 min and then half the shed blood mixed with 100 u/ml heparinised saline i.v. over a period of 50 min. At the end of 1 h resuscitation, an i.v. infusion of Ringer's Lactate (1.5 ml/kg/h) was started as fluid replacement and maintained for a further 3 h.

1.3 Quantification of Organ Injury/Dysfunction

Four hours after the onset of resuscitation, 1.2 ml blood was collected from the right carotid artery and decanted into serum gel tubes (Sarstedt, Numbrecht, Germany), after which the heart was removed to terminate the experiment. The samples were centrifuged (9900 rpm for 3 min) to separate serum from which urea, creatinine, aspartate aminotransferase (AST), alanine aminotransferase (ALT) and creatinine kinase (CK) were measured within 24 hours (Idexx Laboratories Ltd., West Yorkshire, UK). Urine collected during the last 3 h of the experiment was analysed for creatinine levels in order to estimate creatinine clearance as an indicator of glomerular dysfunction and was calculated as follows:

$$\text{Creatinine Clearance (ml/min)} = \frac{\text{urine creatinine (}\mu\text{mol}/l) \times \text{urine flow (ml/min)}}{\text{serum creatinine (}\mu\text{mol}/l)}$$

1.4 Experimental Design

Rats were randomly allocated into the following groups:
(i) Sham (n=4)
(ii) HS Control (n=10)
(iii) HS+Artesunate 1 mg/kg (n=6)
(iv) HS+Artesunate 3 mg/kg (n=7)
(v) HS+Artesunate 10 mg/kg (n=8)

Sham-operated rats underwent identical surgical procedures but without haemorrhage or resuscitation. Animals received either 10% DMSO (1 ml/kg i.v.) or artesunate (1, 3 or 10 mg/kg i.v.) on resuscitation.

1.5 Materials

Unless otherwise stated, all compounds were obtained from Sigma-Aldrich Company Ltd (Poole, Dorset, U.K.). All stock solutions were prepared in non-pyrogenic saline [0.9% (w/v) NaCl: Baxter Healthcare Ltd., Thetford, Norfolk, U.K.]. Ringer's Lactate was also obtained from Baxter Healthcare Ltd. Sodium thiopentone (Thiovet™) was obtained from Link Pharmaceuticals, Horsham, U.K. Multiparin (Heparin injection B.P., 5,000 iu/ml) was obtained from National Veterinary Services, Stoke-on-Trent, U.K., 0.1 ml Multiparin added to 4.9 ml 0.9% (w/v) sodium chloride to give concentration of 100 u/ml and 5 ml Multiparin added to 1 liter 0.9% (w/v) sodium chloride to give concentration of 25 u/ml. Artesunate was also obtained from Sigma-Aldrich Company Ltd (Poole, Dorset, U.K.).

1.6 Statistical Analysis

All values described in the text and figures are expressed as mean±standard error of the mean (SEM) for n observations. Each data point represents biochemical measurements obtained from up to 10 separate animals. Statistical analysis was carried out using GraphPad Prism 5.03 (GraphPad Software, San Diego, Calif., USA). Data without repeated measurements was assessed by one-way ANOVA followed by Dunnett's post hoc test. Data with repeated measurements was assessed by two-way ANOVA followed by Bonferroni's post hoc test. A P value of less than 0.05 was considered to be significant.

Figure 1:
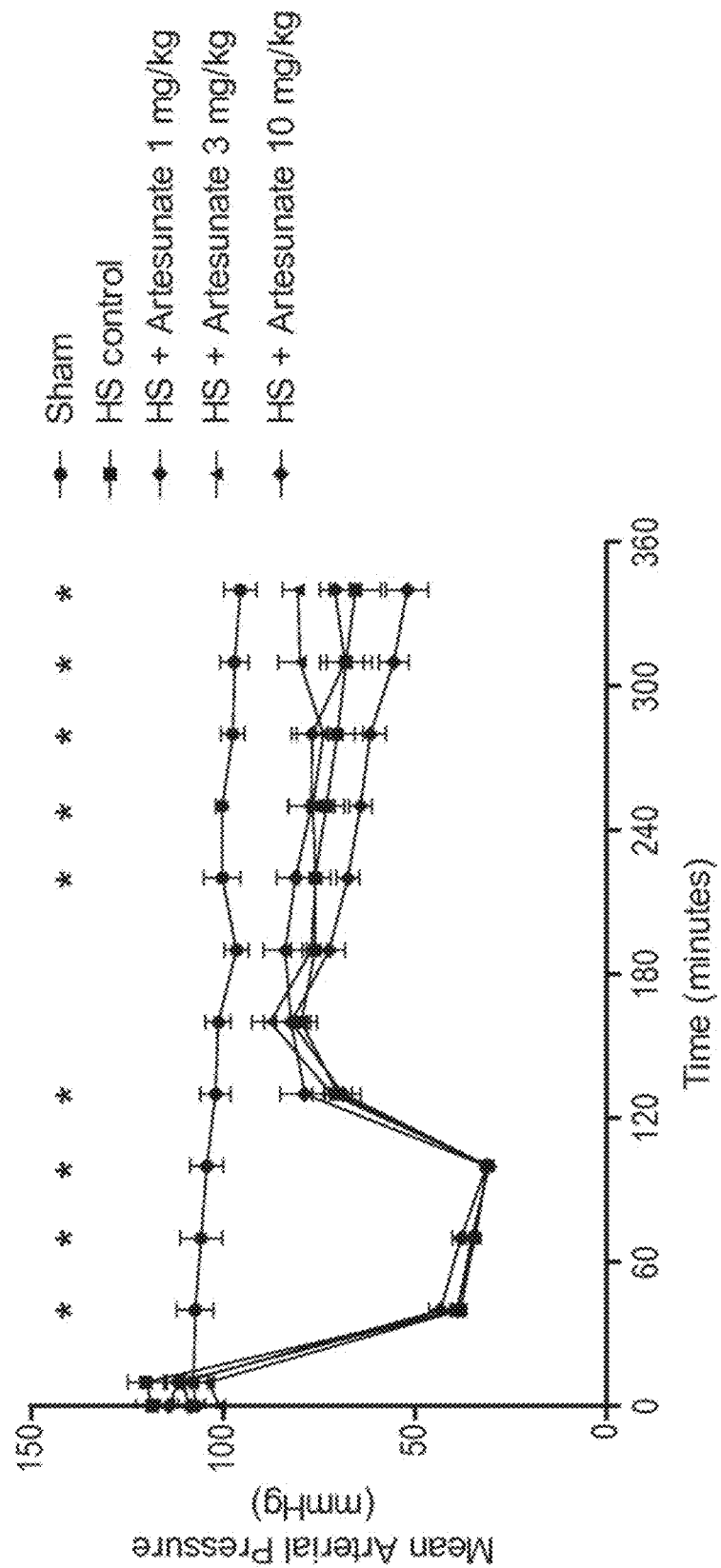

1.7 Effect of Artesunate on the Circulatory Failure Caused by Haemorrhagic Shock When compared to sham-operated rats, HS-rats treated with vehicle demonstrated a significant reduction in MAP during the resuscitation period (P<0.05, FIG. 1). The administration of artesunate (1, 3 or 10 mg/kg) on resuscitation failed to attenuate the decline in MAP caused by haemorrhage during the resuscitation phase (P>0.05, FIG. 1).

Figure 2:
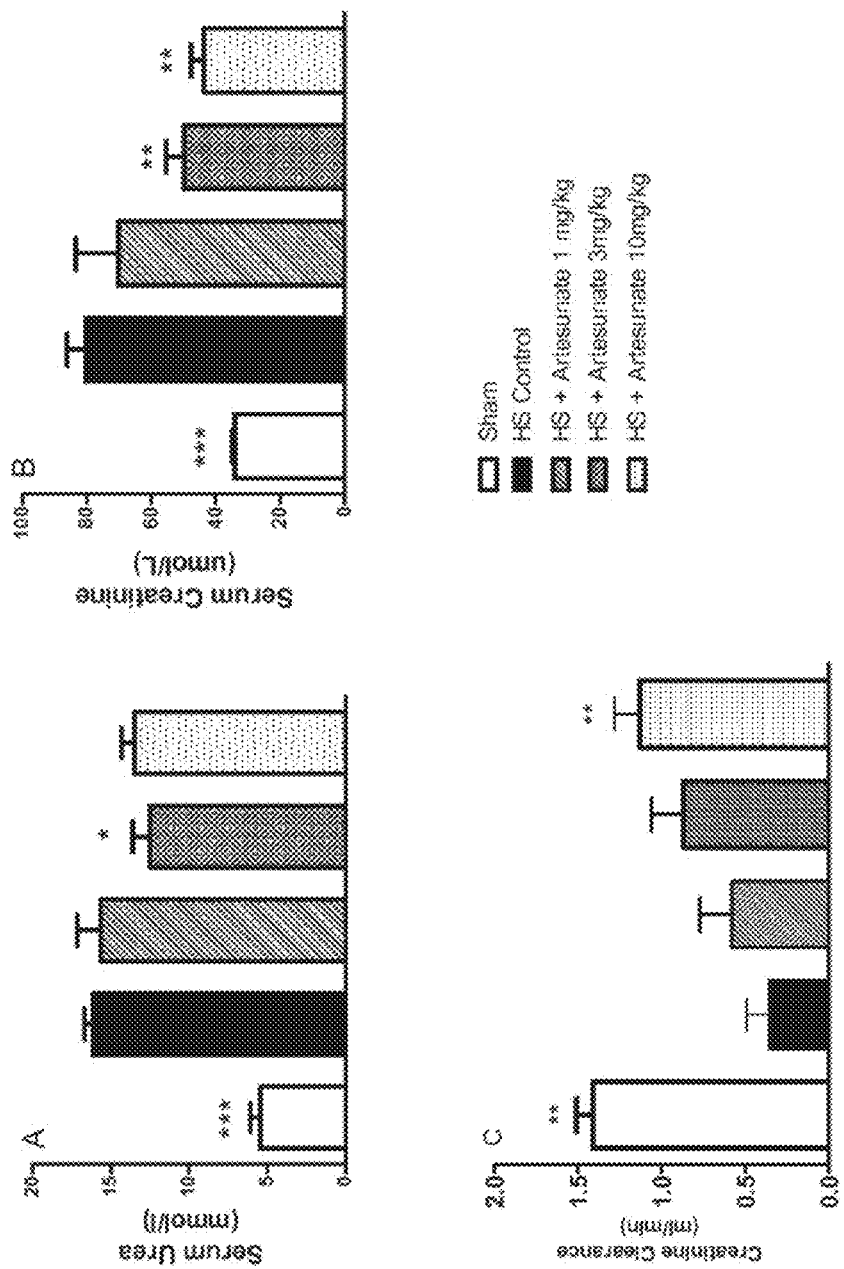

1.8 Effect of Artesunate on the Organ Injury and Dysfunction Induced by Haemorrhagic Shock When compared to sham-operated rats, HS-rats treated with vehicle developed significant increases in serum urea (P<0.001, FIG. 2A) and creatinine (P<0.001, FIG. 2B); creatinine clearance was significantly reduced when compared to sham-operated rats (P<0.005, FIG. 2C) indicating the development of renal and glomerular dysfunction. Treatment of HS-rats with 3 mg/kg artesunate significantly attenuated the rises in serum urea (P<0.05, FIG. 2A) and creatinine (P<0.005, FIG. 2B) when compared to HS-rats; whereas treatment with 10 mg/kg artesunate significantly attenuated the rise in serum creatinine (P<0.005, FIG. 2B) and the fall in creatinine clearance (P<0.005, FIG. 2C). Treatment of HS-rats with 1 mg/kg artesunate had no significant effect on the rises in serum urea (P>0.05, FIG. 2A) and creatinine (P>0.05, FIG. 2B) or on the fall in creatinine clearance (P>0.05, FIG. 2C).

Figure 3:
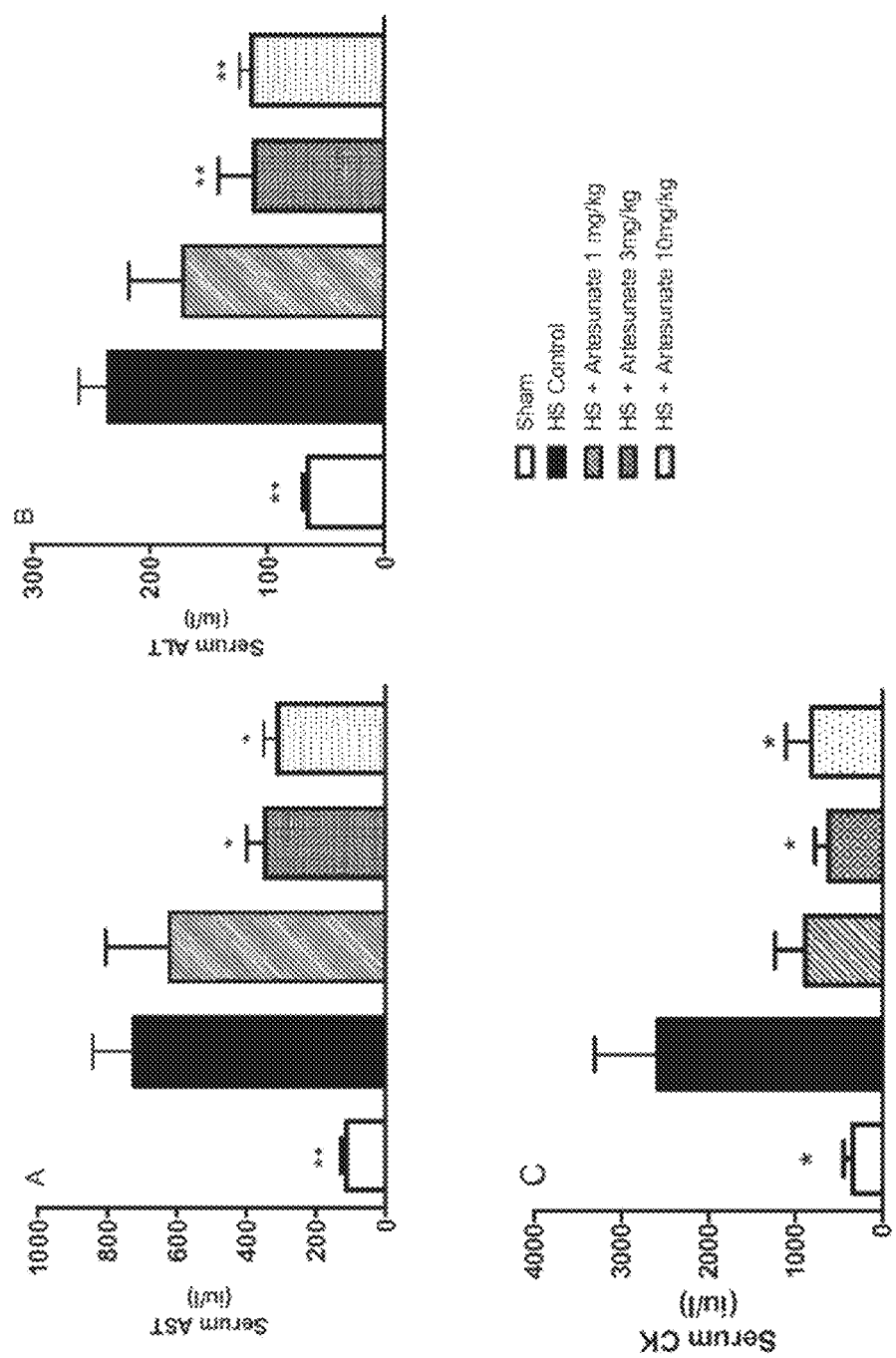

When compared to sham-operated rats, HS-rats treated with vehicle developed significant increases in serum AST (P<0.005, FIG. 3A), ALT (P<0.005, FIG. 3B) and creatinine kinase (P<0.05, FIG. 3C) indicating the development of liver injury and skeletal-muscle injury. Treatment of HS-rats with artesunate (both 3 and 10 mg/kg) significantly attenuated the rises in serum AST (P<0.05, FIG. 3A), ALT (P<0.005, FIG. 3B) and creatinine kinase (P<0.05, FIG. 3C). Treatment with 1 mg/kg artesunate had no significant effect on the rises in serum AST (P>0.05, FIG. 3A), ALT (P>0.05, FIG. 3B) or creatinine kinase (P>0.05, FIG. 3C).

2. Evaluation of the Effects of Artesunate on the Organ Injury and Dysfunction Induced by Burn Injury in the Rat 2.1. Surgical Procedure Twenty-two male Wistar rats (Harlan, Udine, Italy) weighing 300 to 350 g were anaesthetised with sodium pentobarbital (Eutasil™, 60 mg/kg i.p.; Sanofi Veterinária, Algés, Portugal), which was supplemented as required. Anaesthetised rats were shaved (dorsum and abdomen) and placed onto a thermostatically controlled heating mat (Harvard Apparatus Ltd, Kent, U.K.) and body temperature maintained at 37±1° C. by means of a rectal probe attached to a homeothermic blanket. A tracheotomy was performed to maintain airway patency and to facilitate spontaneous respiration. Thirty minutes prior to burn injury, rats were treated with vehicle or drug, as described in section 3.2. To induce burn injury, a 60% third degree skin burn was induced by immersing dorsal shaved skin in 99° C. water for 10 s using a synthetic foam template. The rats were then dried and placed over the heating mat. Rats were sacrificed at 6 hours after burn injury by overdose of the anaesthetic and serum samples obtained for analysis of organ injury and dysfunction.

2.2 Experimental Design

Rats were randomly allocated into the following groups:
(i) Sham (n=4)
(ii) Burn+10% DMSO (n=10)
(iii) Burn+Artesunate (n=9)

Sham-operated rats underwent identical surgical procedures but without burn injury (immersed in room temperature water). Animals received either 10% DMSO (1 ml/kg i.v.) or artesunate (3 mg/kg i.v.) 30 min prior to burn injury and 30 min after burn injury 2.3 Materials Unless otherwise stated, all compounds were obtained from Sigma-Aldrich Química S.A. (Sintra, Portugal). Pentobarbital sodium (Eutasil™) was obtained from Sanofi Veterinária (Miraflores, Algés, Portugal). All stock solutions were prepared in non-pyrogenic saline (0.9% NaCl; B. Braun Medical Lda, Queluz, Portugal).

2.4 Statistical Analysis

Each data point represents measurements obtained from up to 10 separate animals. Data was assessed using Mann-Whitney U test.

2.5 Effect of Artesunate on the Renal Dysfunction Induced by Burn Injury

Figure 4:
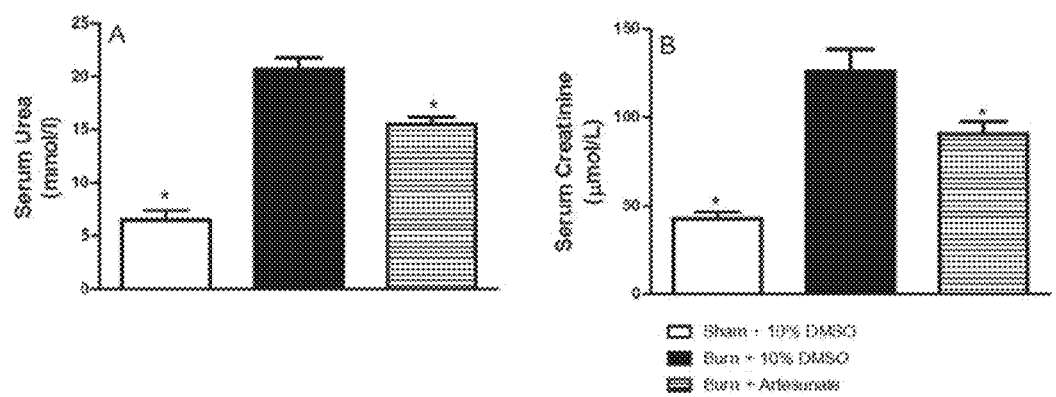
FIGS. 4A and 4B show alterations in serum levels of (a) urea and (b) creatinine, in rats subjected to (i) surgical procedure alone and treated with vehicle (Sham+10% DMSO, n=4), burn injury and treated with (ii) vehicle (Burn+10% DMSO, n=10) or (iii) artesunate (Burn+Artesunate, n=9). Data is expressed as mean±SEM, *$P<0.05$ when compared to Burn+10% DMSO.

When compared to sham-operated rats, rats subjected to burn injury and treated with vehicle developed significant increases in serum urea (P<0.05, FIG. 4A) and creatinine (P<0.05, FIG. 4B) indicating the development of renal dysfunction. Treatment of burn injury rats with 3 mg/kg artesunate significantly attenuated the rises in serum urea (P<0.05, FIG. 4A) and creatinine (P<0.05, FIG. 4B) when compared to burns injury rats.

2.6 Effect of Artesunate on the Hepatic Injury Induced by Burn Injury

Figure 5:
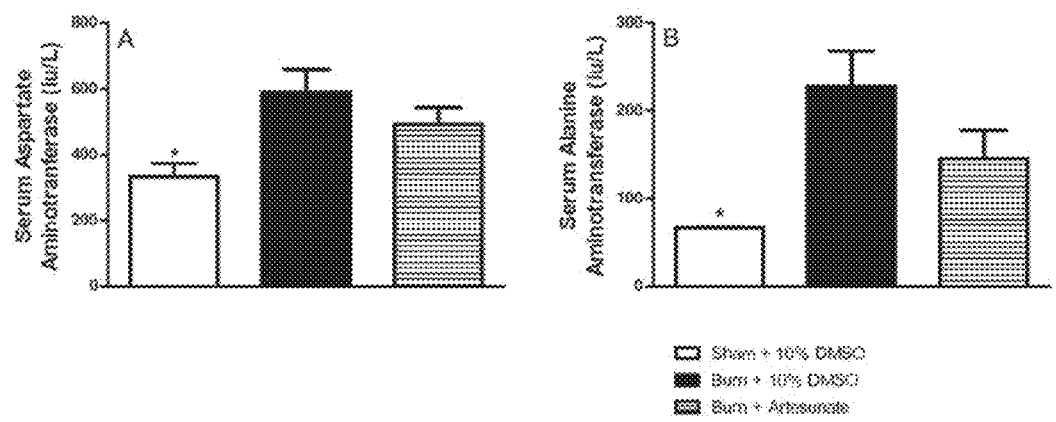
FIGS. 5A and 5B show alterations in serum levels of (a) AST and (b) ALT, in rats subjected to (i) surgical procedure alone and treated with vehicle (Sham+10% DMSO, n=4), burn injury and treated with (ii) vehicle (Burn+10% DMSO, n=10) or (iii) artesunate (Burn+Artesunate, n=9). Data is expressed as mean±SEM, *$P<0.05$ when compared to Burn+10% DMSO.
Figure 6:
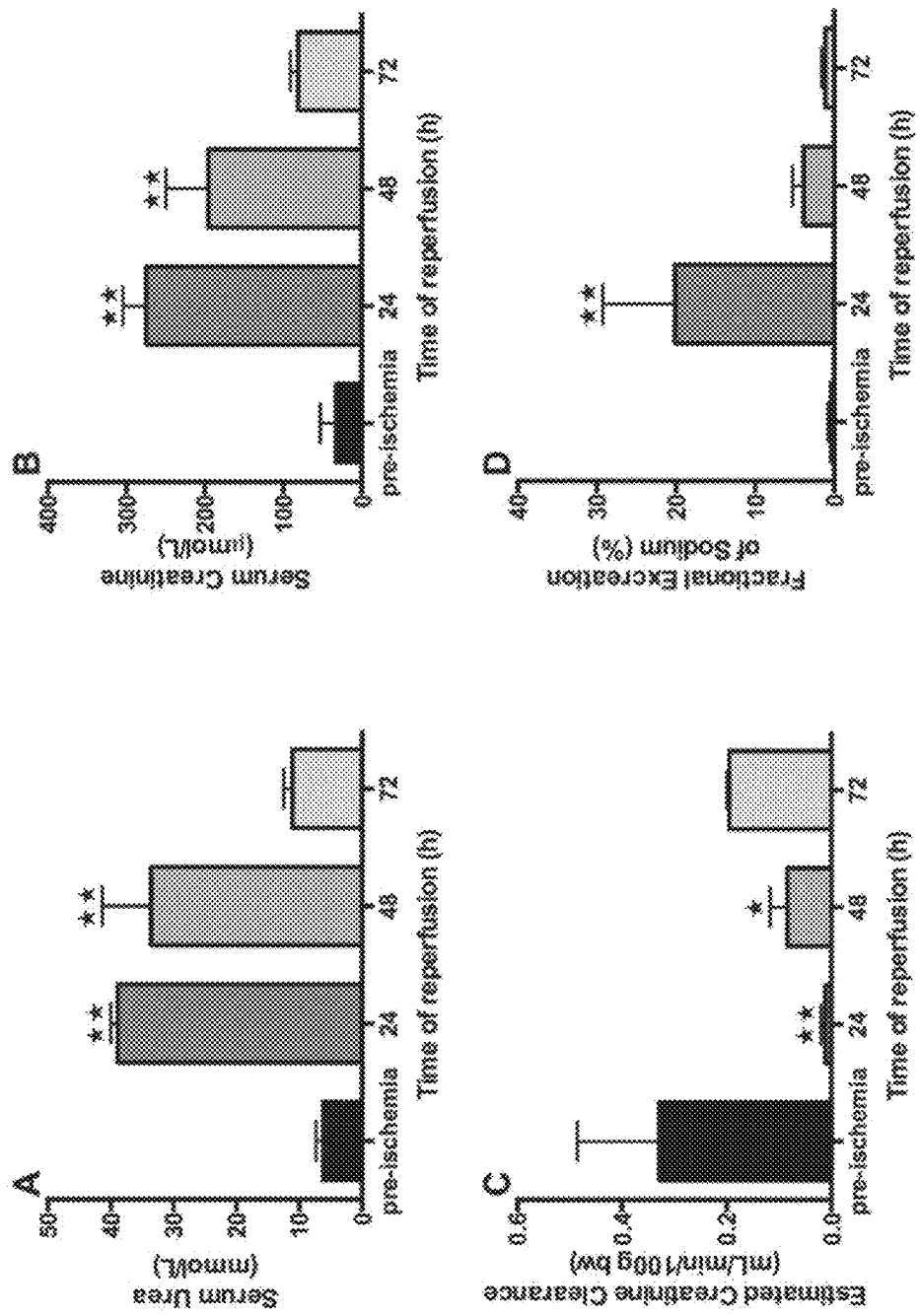
Figure 7:
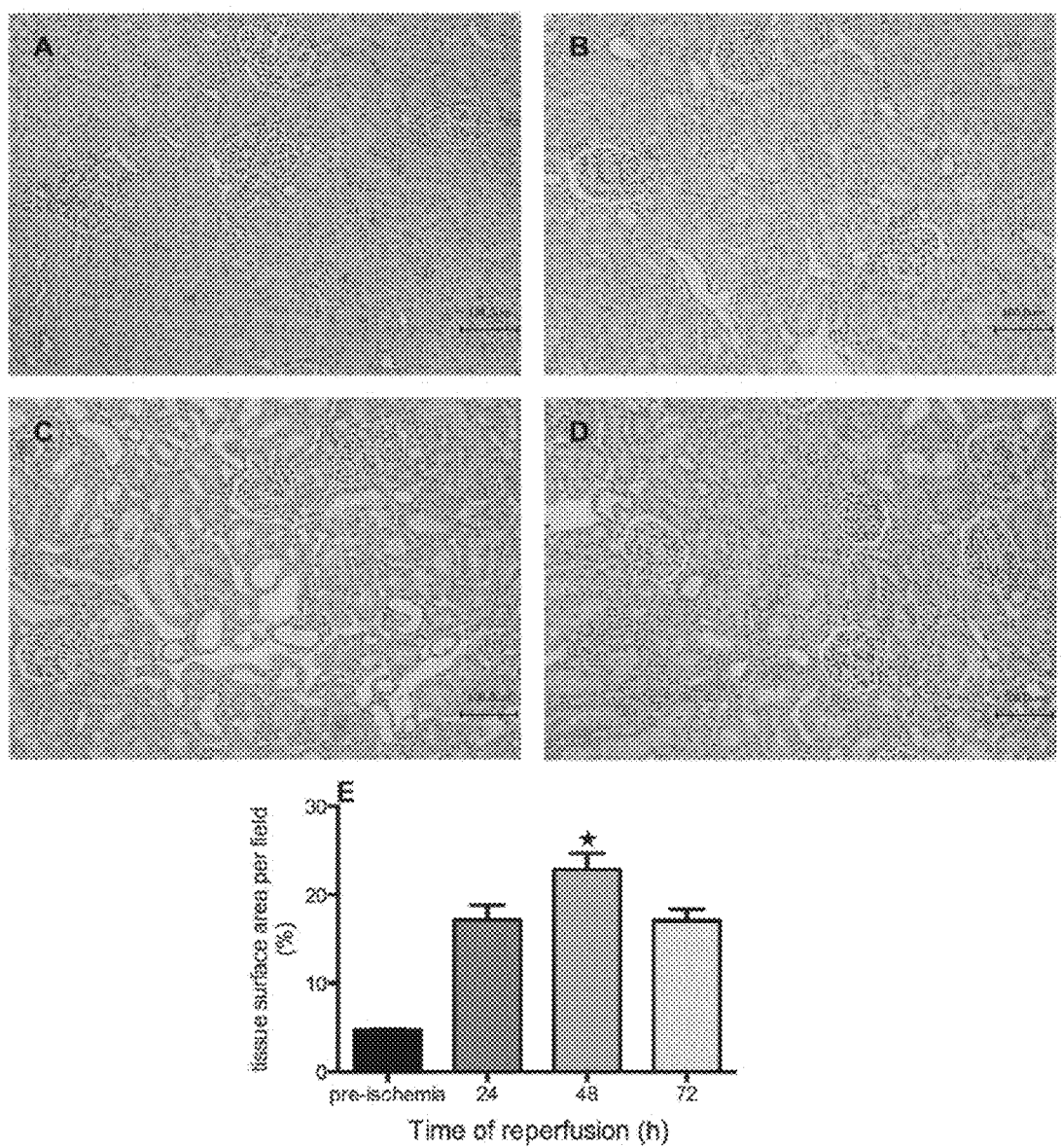

When compared to sham-operated rats, rats subjected to burn injury and treated with vehicle developed significant increases in serum aspartate aminotransferase, AST (P<0.05, FIG. 5A) and alanine aminotransferase, ALT (P<0.05, FIG. 5B) indicating the development of hepatic injury. Treatment of burn injury rats with 3 mg/kg artesunate had no significant effect on the rises in serum AST (P>0.05, FIG. 5A) and ALT (P>0.05, FIG. 5B) induced by burn injury.

2.7 Summary

Treatment of rats subjected burn injury with vehicle resulted in significant renal dysfunction (as indicated by rises in serum urea and creatinine) and significant hepatic injury (as indicated by rises in serum AST and ALT).

Treatment of rats subjected to burn injury with 3 mg/kg artesunate resulted in a significant reduction in the renal dysfunction (measured using serum urea and creatinine) caused by burn injury. However, treatment of rats subjected to burn injury with 3 mg/kg artesunate had no significant effect on the hepatic injury (measured using serum AST and ALT) caused by burn injury.

3.0 Effect of Time on Acute Kidney Injury and the Activation of Intracellular Proteins 3.1 Acute Kidney Injury—Surgical Procedure and Quantification of Organ Injury/Dysfunction This study was carried out on 63 male Wistar rats (Charles River Ltd, Margate, UK) weighing between 240-290 g and receiving a standard diet and water ad libitum. Animals were anesthetized using a ketamine (150 mg/kg) and xylazine (15 mg/kg) mixture i.p. (1.5 ml/kg). The hair was shaved and the skin cleaned with 70% alcohol (v/v). The animals were then placed on a homoeothermic blanket set at 37° C. Animals received 0.1 mg/kg s.c. buprenorphine (0.1 ml/kg) prior to commencement of surgery. A mid-line laparotomy was then performed. The right renal pedicle (consisting of the renal artery, vein and nerve) was isolated and tied off using sterile 4-0 silk-braided suture (Pearsalls Ltd., Taunton, UK). The right kidney was then surgically removed. The left renal pedicle was isolated and clamped using a non-traumatic microvascular clamp at time 0. After 30 min of unilateral renal ischemia, the clamp was removed to allow reperfusion. For reperfusion, the kidneys were observed for a further 5 min to ensure reflow, following which 8 ml/kg saline at 37° C. was injected into the abdomen and all incisions were sutured in two layers (Ethicon Prolene 4-0). Animals were then allowed to recover on the homeothermic blanket and placed into cages upon recovery. Twenty-four hours prior to the end of the experiment, rats were placed in metabolic cages for the collection of urine and the subsequent determination of both estimated creatinine clearance and fractional excretion of sodium. At the end of the experiment, blood was taken by cardiac puncture into non-heparinized syringes and immediately decanted into 1.3 ml serum gel tubes (Sarstedt, Germany). The blood was centrifuged at 9900 g for 5 min to separate serum. All biochemical markers in serum and urine were measured in a blinded fashion by a commercial veterinary testing laboratory (IDEXX Ltd, West Sussex, UK). The left kidney was removed following removal of the heart. Half of the left kidney was snap frozen and stored at −80° C., and the other half was stored in 10% neutral buffered formalin.

3.2 Experimental Design (Time Course)

Rats were randomly allocated into the following groups:
(i) pre-ischemia (n=4); (ii) 24 h reperfusion (n=4); (iii) 48 h reperfusion (n=8); and (v) 72 h reperfusion (n=4).

3.3 Histological Evaluation and Scoring

Kidneys were fixed in 10% neutral buffered formalin for 48 h before being dehydrated with 70% ethanol. Tissues were embedded in paraffin and sections were cut at 4 μm by a single technician in order to minimize variations in section thickness. The slides were deparaffinised with xylene, stained with haematoxylins and eosin and viewed with a Keyence Biozero BZ-8000 microscope (Ontario, Canada). Histological features such as glomerular shrinkage, tubular dilatation, basophilia, necrosis and luminal congestion were noted. Ten random images were taken per slide and quantified for total tissue surface area using ImageJ as a marker of renal injury.

3.4 Western Blot Analysis

Western blots were carried out as previously described [22]. Three separate experiments of western blot analysis were performed for each marker and tissues were done separately for each western blot experiment. Briefly, previously snap frozen rat kidney samples were homogenized and centrifuged at 4,000 g for 5 min at 4° C. Supernatants were removed and centrifuged at 15,000 g at 4° C. for 40 min to obtain the cytosolic fraction. The pelleted nuclei were re-suspended in extraction buffer. The suspensions were centrifuged at 15,000 g for 20 min at 4° C. The resulting supernatants containing nuclear proteins were carefully removed, and protein content was determined using a bicinchoninic acid (BCA) protein assay following the manufacturer's directions. Proteins were separated by 8% sodium dodecyl sulphate-polyacrylamide gel electrophoresis (SDS-PAGE) and transferred to a polyvinyldenedifluoride (PVDF) membrane, which was then incubated with a primary antibody (mouse anti-total I$\kappa$B$\alpha$ dilution 1:1000; mouse anti-pI$\kappa$B$\alpha$ Ser$^{32/36}$ dilution 1:1000; rabbit anti-total eNOS dilution 1:200; goat anti-peNOS Ser$^{1177}$ dilution 1:200; rabbit anti-NF-$\kappa$B p65 dilution 1:1000). Blots were then incubated with a secondary antibody conjugated with horseradish peroxidase (dilution 1:10000) and developed using the ECL detection system. The immunoreactive bands were visualized by autoradiography. The membranes were stripped and incubated with β-actin monoclonal antibody (dilution 1:5000) and subsequently with an anti-mouse antibody (dilution 1:10000) to assess gel-loading homogeneity. Densitometric analysis of the bands was performed using Gel Pro®Analyzer 4.5, 2000 software (Media Cybernetics, Silver Spring, Md., USA) and optical density analysis was expressed as fold-increase versus the sham group. In the sham group, the immunoreactive bands of the gel were respectively measured and normalized against the first immunoreactive band (standard sham sample) and the results of all the bands belonging to the same group were expressed as mean±SEM. This provides SEM for the sham group where a value of 1 is relative to the first immunoreactive band. The membranes were stripped and incubated with β-actin monoclonal antibody and subsequently with an anti-mouse antibody to assess gel-loading homogeneity. Relative band intensity was assessed and normalized against parallel β-actin expression. Each group was then adjusted against corresponding Sham data to establish relative protein expression when compared to Sham animals.

3.5 Materials

Unless otherwise stated, all compounds used in this study were purchased from Sigma-Aldrich Company Ltd. (Poole, Dorset, U.K.). All stock solutions were prepared using non-pyrogenic saline (0.9% [w/v] NaCl; Baxter Healthcare Ltd., Thetford, Norfolk, U.K.). Ringer's Lactate was purchased from Baxter Healthcare Ltd. Antibodies for western blot analysis were purchased from Santa Cruz Biotechnology, Inc. (Heidelberg, Germany).

3.6 Statistical Analysis

All values described in the text and figures are expressed as mean±standard error of the mean (SEM) for n observations. Each data point represents biochemical measurements obtained from up to 11 separate animals. Statistical analysis was carried out using GraphPad Prism 6.0b (GraphPad Software, San Diego, Calif., USA). Data without repeated measurements was assessed by one-way ANOVA followed by Bonferroni's multiple-comparison post hoc test. A P value of less than 0.05 was considered to be significant.

3.7 Results

When compared to baseline (pre-ischemia), rats that underwent 30 min of unilateral renal ischemia developed significant renal (as measured by rises in serum urea and creatinine), glomerular (as measured by a fall in estimated creatinine clearance) and tubular dysfunction (as measured by a rise in fractional excretion of sodium) at 24 h of reperfusion, followed by a progressive recovery of renal, glomerular and tubular function without intervention (FIGS. 6a, 6B, 6C, and 6D). When compared to baseline (pre-ischemia), rats that underwent 30 min of unilateral renal ischemia developed histological signs of significant renal injury (see methods) at 48 h of reperfusion (FIGS. 7A, 7B, 7C, 7D, and 7E). These findings indicate the development of acute kidney injury. When compared to baseline (pre-ischemia), rats that underwent 30 min of unilateral renal ischemia developed significant phosphorylation of Ser32/36 on I$\kappa$B$\alpha$ and, hence, activation of the IKK complex, at 48 h of reperfusion (FIG. 8A). Subsequently, activation of the IKK complex resulted in significant nuclear translocation of the NF-$\kappa$B subunit p65 at 48 h of reperfusion (FIG. 8B). In addition, at 48 h of reperfusion the phosphorylation of Ser1177 on eNOS was significantly reduced when compared to baseline (FIG. 8C).

4.0 Effect of Late Administration of Artesunate in a Recovery Rat Model of Unilateral Renal Ischaemia/Reperfusion Injury

4.1 Surgical Procedure

Thirty-one male Wistar rats (240-270 g, Charles River, Margate, U.K.) were used in this study. Rats were anaesthetised with a ketamine (100 mg/ml) and xylazine (20 mg/ml) mixture (2:1; 1.5 ml/kg, i.p.) and anaesthesia was maintained by supplementary injections (200 μg/kg i.p.) of ketamine/xylazine. Buprenorphine was administered at a dose of 0.1 mg/kg s.c. (0.5 ml/kg). Rats were then, placed onto a thermostatically controlled heating mat (Harvard Apparatus Ltd., Kent, U.K.) set at 37° C. A midline laparotomy was then performed. The anatomical right kidney was removed following permanent ligation of the renal artery and vein. The left renal pedicle (consisting of the renal artery, vein and nerve) was isolated and clamped using a non-traumatic microvascular clamp at time 0 for 30 min. Body temperature was maintained at 35±1° C. during ischaemia by means of measuring rectal temperature with a thermometer. After 30 min of unilateral renal ischaemia, the clamp was removed to allow reperfusion for 48 h. After the renal clamp were removed, the kidney were observed for a further 5 min to ensure reflow after which 2 ml saline at 37° C. was injected into the abdomen and all incisions were sutured in two layers. Rats were then allowed to recover from anaesthesia on the homoeothermic blanket and placed back into cages. Twenty-four hours prior to sacrifice rats were individually placed into metabolic cages for the collection of urine. Rats were re-anaesthetised with sodium thiopentone (120 mg/kg i.p., LINK Pharmaceuticals Ltd., West Sussex, UK) at the end of 48 h reperfusion.

4.2 Sample Collection

For the time-course experiments serial blood samples were collected from rats over the course of the reperfusion phase. Following the reperfusion period, ~3.5 ml of blood was taken from the right ventricle of the heart via cardiac puncture into non-heparinised 5 ml syringes and immediately decanted into 1.3 ml serum gel tubes (Sarstedt, Germany). The blood was centrifuged at 9900 g for 3 min to separate serum, which was subsequently stored at −80° C. until analysis. The lungs, liver and kidney were excised of which one section of each organ was snap frozen in liquid nitrogen and stored at −80° C. and the other was placed in 10% formalin until analysis (if required). All biochemical markers in serum and urine were measured in a blinded fashion by a commercial veterinary testing laboratory (IDEXX Ltd, West Sussex, UK). Serum urea and creatinine are used as indicators of renal dysfunction. Creatinine clearance is used as an indicator of glomerular dysfunction and is calculated as follows $$\text{Creatinine Clearance (ml/min)} = \frac{\text{urine creatinine (μmol/}l\text{)} \times \text{urine flow (ml/min)}}{\text{serum creatinine (μmol/}l\text{)}}$$

Fractional excretion of sodium is used as an indicator of tubular dysfunction and is calculated as follows:

$$\text{Fractional Excretion of Sodium (\%)} = \frac{\text{urine sodium (mmol/}l\text{)} \div \text{serum sodium (mmol/}l\text{)}}{\text{urine creatinine (μmol/}l\text{)} \div \text{serum creatinine (μmol/}l\text{)}}$$

4.3 Experimental Design

Animals were randomised into seven experimental groups and treated with either sodium bicarbonate as a 1 ml/kg i.v. bolus 24 h into reperfusion or artesunate at 0.3 mg/kg as an i.v. bolus 24 h into reperfusion (see Tables 2 and 3, where n represents the number of animals studied).

TABLE 2

Experimental Design for Characterisation of Acute Kidney Injury in a Rat Model of Unilateral Renal Ischaemia/Reperfusion Injury

| Group | Treatment | Protocol Ischaemia (min) | Reperfusion (h) | n |
|---|---|---|---|---|
| A | Baseline | — | — | 4 |
| B | 24 h | 30 | 24 | 4 |
| C | 48 h | 30 | 48 | 8 |
| D | 72 h | 30 | 72 | 4 |

TABLE 3

Experimental Design for Treatment with Artesunate in a Rat Model of Unilateral Renal Ischaemia/Reperfusion Injury

| Group | Treatment | Bolus Conc. (mg/mL) | 24 h into reperfusion Dose (mg/kg) | Dose Volume (ml/kg) | n |
|---|---|---|---|---|---|
| E | Sham + Vehicle | Sodium Bicarbonate | — | 1 | 8 |
| F | IRI + Vehicle | Sodium Bicarbonate | — | 1 | 8 |
| G | IRI + Artesunate | 0.3 | 0.3 | 1 | 7 |

4.4 Materials and Drug Preparation

Sodium bicarbonate was purchased from Sigma-Aldrich Co Ltd and stored as 10 ml tubes at −20° C. Saline was obtained from Baxter Healthcare Ltd (UKF7124). Artesunate (Guilin Pharmaceuticals Co Ltd, China) was prepared prior to the start of the study in 3 mg/ml aliquots and stored at −20° C. for no longer than one month. On the day of injection one aliquot was removed from the freezer and diluted to the required concentration (see below).

Artesunate 0.3 mg/kg:

i.v. Bolus Dose 0.3 mg/kg

Compound is administered in a volume of 1 ml/kg.

Therefore, concentration of the compound assuming each rat weighs 250 g is:

p.o. Bolus Concentration=0.3 mg/ml

Concentration of stock=3 mg/ml in 1 ml aliquots.

Dilution factor: 3÷0.3=10

Allow 1 ml per rat for a Bolus Dose, i.e. 100 μl of 3 mg/ml artesunate stock required per 900 μl of sodium bicarbonate.

4.5 Statistical Evaluation

All data in the text and figures are presented as mean±SEM of n observations, where n represents the number of animals studied. All statistical analysis was calculated using GraphPad Prism 6 (GraphPad Software, San Diego, Calif., USA). Biochemical data was analysed by one-way ANOVA for data representing more than two groups, followed by a Dunnett's post hoc test for comparison of sham/treated groups with the control vehicle. A P-value of less than 0.05 was considered to be statistically significant.

Figure 9:
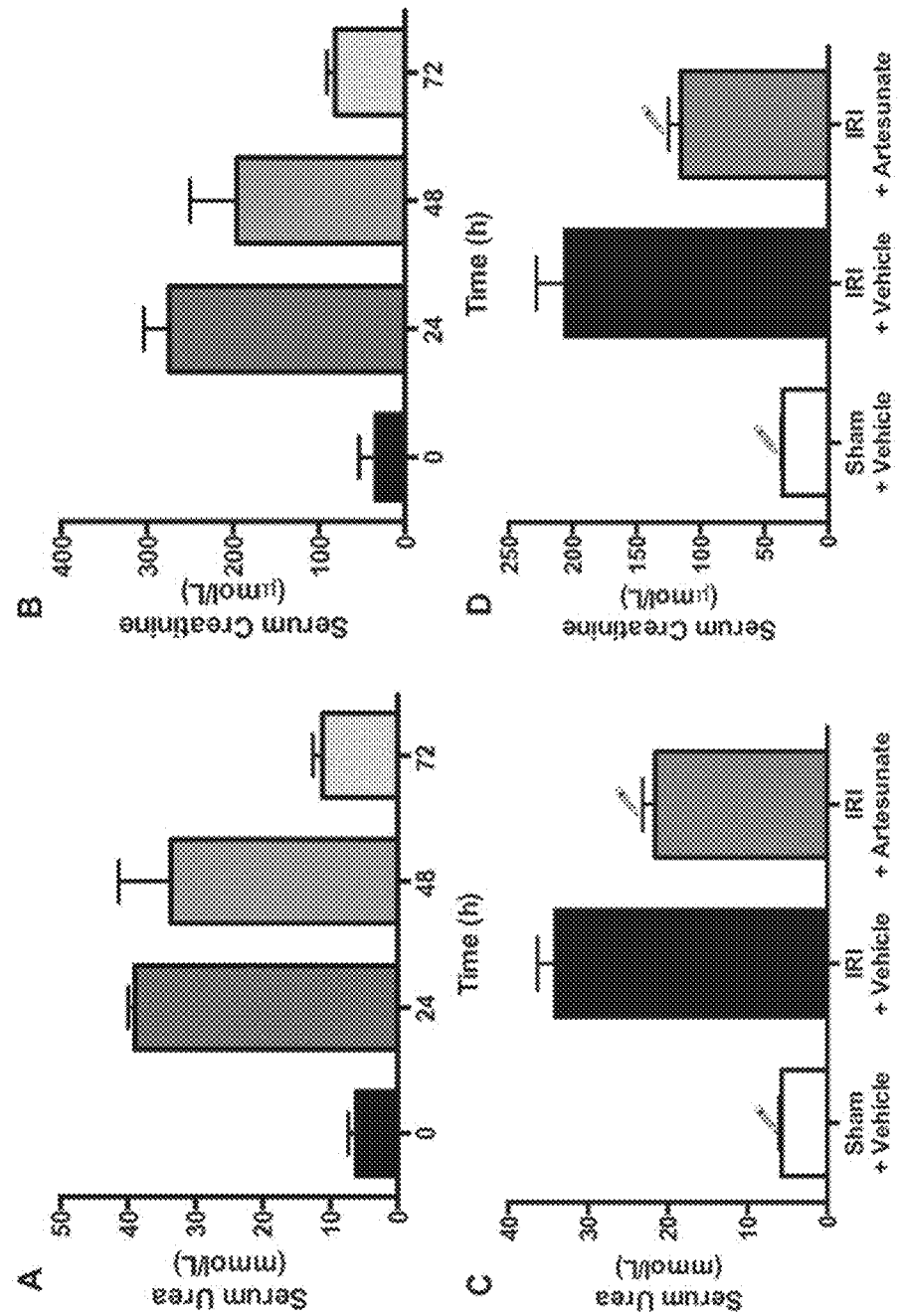

4.6 Effects of Time and Artesunate on the Renal Dysfunction Caused by Ischaemia and Reperfusion When compared to baseline (0 h of reperfusion), rats that underwent 30 min of unilateral renal ischaemia developed a peak of renal dysfunction at 24 h of reperfusion, followed by a progressive recovery of renal function without intervention (FIGS. 9A and 9B).

When compared sham-operated rats, rats that underwent 30 min of unilateral renal ischaemia and 48 h of reperfusion exhibited a significant increase in serum urea from 5.75±0.28 to 34.13±2.23 mmol/L (P<0.05, FIG. 9C) and serum creatinine from 35.60±1.26 to 205.90±22.23 μmol/L (P<0.05, FIG. 9D). These findings indicate the development of acute kidney injury. Compared to rats subjected to ischaemia/reperfusion only, treatment with 0.3 mg/kg artesunate 24 h into reperfusion (the peak of dysfunction) significantly attenuated serum urea from 34.13±2.23 to 21.63±1.51 mmol/L (P<0.05, FIG. 9C) and serum creatinine from 205.90±22.23 to 115.4±9.72 μmol/L (P<0.05, FIG. 9D).

4.7 Effects of Time and Artesunate on the Glomerular Dysfunction Caused by Ischaemia and Reperfusion When compared to baseline (0 h of reperfusion), rats that underwent 30 min of unilateral renal ischaemia developed a peak of glomerular dysfunction at 24 h of reperfusion, followed by a progressive recovery of glomerular function without intervention (FIG. 10A).

When compared sham-operated rats, rats that underwent 30 min of unilateral renal ischaemia and 48 h of reperfusion exhibited a significant increase in estimated creatinine clearance from 0.51±0.02 to 0.08±0.01 ml/min/100 g bw (P<0.05, FIG. 10B) These findings indicate the development of acute kidney injury. Compared to rats subjected to ischaemia/reperfusion only, treatment with 0.3 mg/kg artesunate 24 h into reperfusion (the peak of dysfunction) significantly attenuated estimated creatinine clearance from 0.08±0.01 to 0.14±0.02 ml/kg/100 g bw (P<0.05, FIG. 10B).

4.8 Effects of Time and Artesunate on the Tubular Dysfunction Caused by Ischaemia and Reperfusion When compared to baseline (0 h of reperfusion), rats that underwent 30 min of unilateral renal ischaemia developed a peak of tubular dysfunction at 24 h of reperfusion, followed by a progressive recovery of tubular function without intervention (FIG. 11A).

When compared sham-operated rats, rats that underwent 30 min of unilateral renal ischaemia and 48 h of reperfusion exhibited a significant increase in fractional excretion of sodium from 0.59±0.07 to 4.45±0.65% (P<0.05, FIG. 11B) These findings indicate the development of acute kidney injury. Compared to rats subjected to ischaemia/reperfusion only, treatment with 0.3 mg/kg artesunate 24 h into reperfusion (the peak of dysfunction) significantly attenuated fractional excretion of sodium from 4.45±0.65 to 1.90±0.17% (P<0.05, FIG. 11B).

4.9 Summary and Conclusions

Rats subjected to unilateral renal ischemia for 30 min, following right kidney nephrectomy, developed transient increases in renal dysfunction (as indicated by a rise in serum creatinine and urea), glomerular dysfunction (as indicated by a decline in estimated creatinine clearance) and tubular dysfunction (as indicated by a rise in fractional excretion of sodium). The peak of dysfunction occurred 24 h after the onset of reperfusion, which progressively declined and resulted in recovery of function 72 h after the onset of reperfusion.

Treatment with artesunate at a dose of 0.3 mg/kg (i.v.) at the peak of renal, glomerular and tubular dysfunction (24 h after the onset of reperfusion) resulted within 24 h in a significant improvement in renal, glomerular and tubular function.

The invention claimed is:

1. A method of treating acute kidney injury or a method of treating acute kidney injury in a patient undergoing kidney dialysis or surgery that results in ischaemia-reperfusion of the whole or part of the kidney, kidney transplantation surgery, kidney and pancreas transplantation surgery, or coronary artery bypass surgery comprising administering a compound according to Formula I

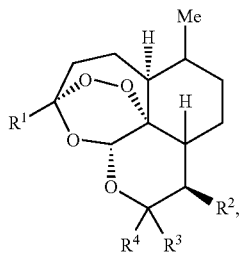

Formula I or a pharmaceutically acceptable salt or ester thereof, or a pharmaceutical composition comprising the compound according to Formula I or a pharmaceutically acceptable salt or ester thereof wherein the pharmaceutical composition further comprises a pharmaceutically acceptable excipient, to a patient in need thereof, wherein:

$R^1$ and $R^2$ are independently H or an optionally substituted group selected from an alkyl, a heteroalkyl, an aryl, a heteroaryl, an arylalkyl, and a heteroarylalkyl; and $R^3$ and $R^4$ taken together form a carbonyl (=O); or $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; and further wherein:

a) the compound or pharmaceutical composition is administered to the patient at least 12 hours after ischaemia-reperfusion of the whole or part of the kidney or at least 12 hours after kidney transplantation surgery, kidney and pancreas transplantation surgery, or coronary artery bypass surgery;

b) the compound or pharmaceutical composition is administered to the patient after diagnosis of acute kidney injury or after diagnosis of a risk of acute kidney injury;

c) the method further comprises measuring serum creatinine levels after surgery and administering the compound or pharmaceutical composition only if acute kidney injury is diagnosed or if the patient is deemed at risk of developing acute kidney injury; or d) the patient is undergoing kidney transplantation, wherein the composition comprising the compound of Formula I, or pharmaceutically acceptable salt or ester thereof, is a reperfusion solution, wherein the reperfusion solution further comprises one or more volume expanders, and wherein the method further comprises bathing the donor kidney in or reperfusing the donor kidney with the reperfusion solution.

2. The method according to claim 1, wherein the compound or pharmaceutical composition is administered at least 12 hours after acute kidney injury.

3. The method according to claim 1, wherein:

$R^1$ and $R^2$ are independently H or an optionally substituted $C_1$-$C_{10}$ alkyl; and $R^3$ and $R^4$ taken together form a carbonyl (=O) group; or $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

4. The method according to claim 1, wherein:

$R^1$ and $R^2$ are independently H or an optionally substituted $C_1$-$C_3$ alkyl; and $R^3$ and $R^4$ taken together form a carbonyl (=O) group; or $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

5. The method according to claim 1, wherein:

$R^1$ and $R^2$ are independently H or an optionally substituted methyl; and $R^3$ and $R^4$ taken together form a carbonyl (=O) group; or $R^3$ is H and $R^4$ is —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

6. The method according to claim 1, wherein:
$R^1$ and $R^2$ are both independently methyl; and
$R^3$ and $R^4$ taken together form a carbonyl (=O) group; or $R^3$ is H and $R^4$ is —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

7. The method according to claim 1, wherein $R^5$ is H, an alkyl, or an arylalkyl, wherein the alkyl and/or arylalkyl is/are optionally substituted with one more or more of halo, =O, $COOR^6$, $OR^6$ and $OCOR^6$, wherein $R^6$ is H or a $C_1$-$C_6$ alkyl.

8. The method according to claim 1, wherein $R^5$ is selected from the group consisting of H, —$CH_3$, —$CH_2CH_3$, —$CO(CH_2)_2COOH$ and —$CH_2C_6H_4COOH$.

9. The method according to claim 1, wherein the compound is selected from the group consisting of artesunate, artemisinin, artemether, dihydroartemisinin, artelinic acid and artemotil.

10. The method according to claim 1, wherein the pharmaceutical composition further comprises an additional pharmaceutically active agent.

11. The method according to claim 1, wherein the compound or composition is administered simultaneously with, separately from, or sequentially to the administration of one or more further pharmaceutically active agents.

12. The method according to claim 1, wherein the compound or pharmaceutical composition is administered by the oral, parenteral, intravenous, intramuscular, intrathecal or intraperitoneal route, or is administered by inhalation.

13. The method according to claim 1, wherein the compound or pharmaceutical composition is administered to the patient at least 12 hours after ischaemia-reperfusion of the whole or part of the kidney or at least 12 hours after kidney transplantation surgery, kidney and pancreas transplantation surgery, or coronary artery bypass surgery.

14. The method according to claim 1, wherein the compound or pharmaceutical composition is administered to the patient after diagnosis of acute kidney injury or after diagnosis of a risk of acute kidney injury.

15. The method according to claim 1, wherein the method further comprises measuring serum creatinine levels after surgery and administering the compound or pharmaceutical composition only if acute kidney injury is diagnosed or if the patient is deemed at risk of developing acute kidney injury.

16. The method of claim 15, wherein the serum creatinine levels are measured at least 12 hours after surgery.

17. The method of claim 15, wherein the acute kidney injury is diagnosed or the patient is deemed at risk of developing acute kidney injury when the serum concentration of creatinine is greater than 1.5 mg/dl.

18. The method according to claim 1 in a patient undergoing kidney transplantation, wherein the composition comprising the compound of Formula I, or pharmaceutically acceptable salt or ester thereof, is a reperfusion solution, wherein the reperfusion solution further comprises one or more volume expanders, and wherein the method further comprises bathing the donor kidney in or reperfusing the donor kidney with the reperfusion solution.

19. The method of claim 18, wherein the volume expander is a colloid or a crystalloid.

20. The method of claim 19, wherein the colloid comprises an aqueous solution comprising at least one component selected from the group consisting of gelatin, succinylated gelatin, albumin, dextran, blood and etherified starch.

21. The method of claim 19, wherein the crystalloid is an aqueous solution comprising at least three ions selected from the group consisting of sodium ions, chloride ions, lactate ions, potassium ions and calcium ions.

22. A method of perfusing a kidney comprising bathing the kidney in a reperfusion solution comprising a compound according to Formula I

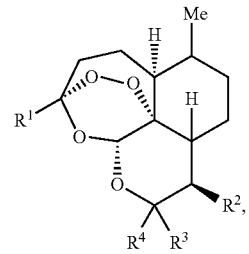

Formula I or a pharmaceutically acceptable salt or ester thereof, and one or more volume expanders, wherein:
$R^1$ and $R^2$ are independently H or an optionally substituted group selected from an alkyl, a heteroalkyl, an aryl, a heteroaryl, an arylalkyl, and a heteroarylalkyl; and
$R^3$ and $R^4$ taken together form a carbonyl (=O); or $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl.

23. The method according to claim 22 further comprising implanting the kidney into a patient.

24. The method of claim 1, wherein the compound is administered by or during kidney dialysis.

* * * * *